US012150916B2

(12) United States Patent
Hines

(10) Patent No.: US 12,150,916 B2
(45) Date of Patent: *Nov. 26, 2024

(54) AUTOMATIC PILL DISPENSER AND METHODS FOR AUTOMATIC PILL DISPENSING

(71) Applicant: Dose Health LLC, New Brighton, MN (US)

(72) Inventor: Paul Hines, New Brighton, MN (US)

(73) Assignee: Dose Health LLC, New Brighton, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/242,831

(22) Filed: Sep. 6, 2023

(65) Prior Publication Data

US 2024/0058219 A1  Feb. 22, 2024

Related U.S. Application Data

(63) Continuation of application No. 17/810,947, filed on Jul. 6, 2022, now Pat. No. 11,793,726, which is a continuation of application No. 17/048,271, filed as application No. PCT/US2019/021494 on Mar. 8, 2019, now Pat. No. 11,432,999.

(60) Provisional application No. 62/658,028, filed on Apr. 16, 2018.

(51) Int. Cl.
*A61J 7/00* (2006.01)
*A61B 5/00* (2006.01)
*A61J 1/03* (2023.01)
*G06F 3/041* (2006.01)

(52) U.S. Cl.
CPC .......... *A61J 7/0076* (2013.01); *A61B 5/4833* (2013.01); *A61B 5/7435* (2013.01); *A61J 1/03* (2013.01); *G06F 3/0412* (2013.01)

(58) Field of Classification Search
CPC ......... A61J 7/0076; A61J 1/03; A61B 5/4833; A61B 5/7435; G06F 3/0412
See application file for complete search history.

(56) References Cited

U.S. PATENT DOCUMENTS

| | | | | |
|---|---|---|---|---|
| 4,572,403 A | * | 2/1986 | Benaroya | A61J 7/04 221/76 |
| 4,748,600 A | * | 5/1988 | Urquhart | A61J 7/049 368/10 |
| 6,601,729 B1 | | 8/2003 | Papp | |
| 6,988,634 B2 | | 1/2006 | Varis | |
| D806,380 S | | 1/2018 | Hines et al. | |
| 10,292,906 B1 | * | 5/2019 | Gershoni | B65D 83/0454 |
| 10,369,081 B2 | | 8/2019 | Hines | |

(Continued)

OTHER PUBLICATIONS

International Preliminary Report on Patentability, International Application No. PCT/US2019/021494, mailing date Oct. 29, 2020.

(Continued)

*Primary Examiner* — Michael Collins
(74) *Attorney, Agent, or Firm* — Merchant & Gould P.C.

(57) ABSTRACT

A portable, versatile pill dispensing system can be used in a variety of settings and for a variety of pill dispensing regimens. Such systems and methods can be configured for intuitive filling or refilling, early or flexible dispensing, remote monitoring software to verify user compliance with a predetermined medication regimen, and features designed to improve compliance while traveling.

19 Claims, 25 Drawing Sheets

(56) References Cited

U.S. PATENT DOCUMENTS

| | | | |
|---|---|---|---|
| 10,596,072 B2 | 3/2020 | Hines | |
| 11,116,699 B2 | 9/2021 | Hines | |
| 11,432,999 B2* | 9/2022 | Hines | G07F 17/0092 |
| 11,793,726 B2* | 10/2023 | Hines | A61J 7/0076 |
| 2003/0127463 A1* | 7/2003 | Varis | G16H 20/13 |
| | | | 221/13 |
| 2006/0102646 A1* | 5/2006 | Godlewski | G07F 11/54 |
| | | | 221/76 |
| 2008/0059228 A1* | 3/2008 | Bossi | G16H 30/20 |
| | | | 705/2 |
| 2012/0006700 A1 | 1/2012 | Geboers et al. | |
| 2014/0025199 A1* | 1/2014 | Berg | G07F 17/0092 |
| | | | 700/232 |
| 2014/0278510 A1* | 9/2014 | McLean | G16H 20/13 |
| | | | 705/2 |
| 2015/0359711 A1 | 12/2015 | Ducatt et al. | |
| 2017/0354574 A1 | 12/2017 | Feng et al. | |
| 2018/0064608 A1 | 3/2018 | Hines | |
| 2018/0064609 A1* | 3/2018 | Hines | G16H 40/67 |
| 2018/0147120 A1 | 5/2018 | Poirier et al. | |
| 2019/0133888 A1 | 5/2019 | Lam | |
| 2019/0307647 A1 | 10/2019 | Greenspan et al. | |
| 2020/0345721 A1 | 11/2020 | Iorio | |

OTHER PUBLICATIONS

Supplementary European Search Report, Application No. 19788377.01, mailed Feb. 23, 2022.

* cited by examiner

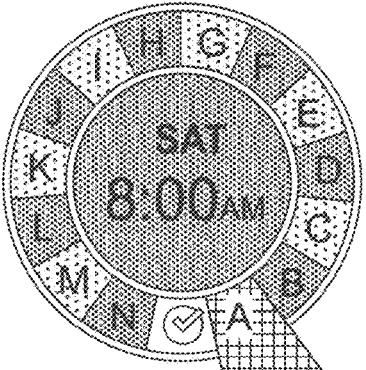
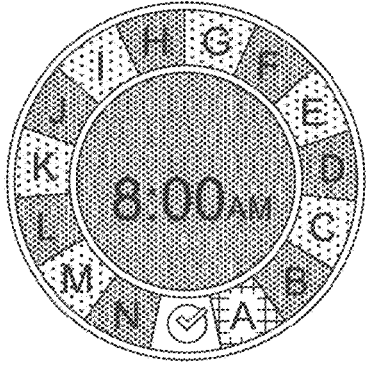
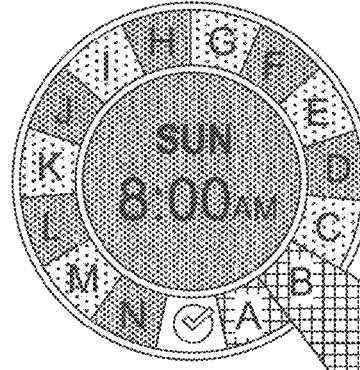
Place all 8:00am pills in each space | Place all 8:00am pills in each space | Place all 8:00am pills in each space
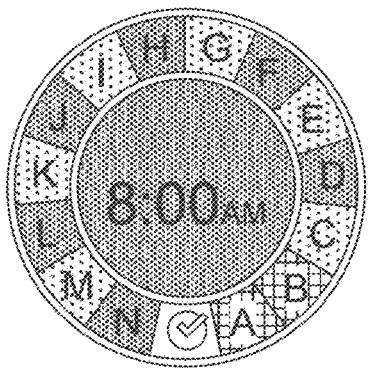
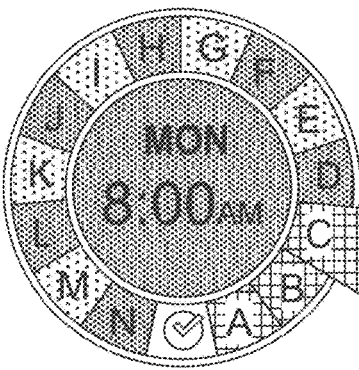
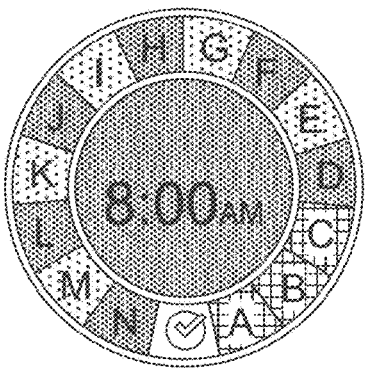
Place all 8:00am pills in each space | Place all 8:00am pills in each space | Place all 8:00am pills in each space
FIG. 6D

| ≡ My Devices | | | | | |
|---|---|---|---|---|---|
| ⊚ All Devices ↙ Statistics | | | | | ((• CONNECT PILLBOX |
| USER | | PILLBOX | SCHEDULE | STATUS | ADHERENCE ⌄ |
| ★ | Name 1 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 75%<br>2139 Dispensed/ 12 Missed |
| ☆ | Name 2 | [A][B][C][D][E][F][G][H][I][J][K][L][M][N]<br>Empty on 1/29/18 7:00pm | 8:30am<br>Local Time: 6:32am PST | ((• CONNECTED<br>1/22/18 2:33pm | 96%<br>2139 Dispensed/ 12 Missed |
| ☆ | Name 3 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |
| ☆ | Name 4 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |
| ☆ | Name 5 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |
| ☆ | Name 6 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |
| ☆ | Name 7 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |
| ☆ | Name 8 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |
| ☆ | Name 9 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |
| ☆ | Name 10 | [A][B][C][D][E][F][G][H][I][J][K][L][M][N]<br>Empty on 1/29/18 3:00pm | 7:00am 11:00pm<br>Local Time: 6:32am PST | ((• CONNECTED<br>1/22/18 2:33pm | 96%<br>2139 Dispensed/ 12 Missed |

AUTOMATIC PILL DISPENSER AND METHODS FOR AUTOMATIC PILL DISPENSING

RELATED APPLICATION

This application is a continuation application of U.S. patent application Ser. No. 17/810,947, filed Jul. 6, 2022, which is a continuation of U.S. patent application Ser. No. 17/048,271, filed Oct. 16, 2020, now issued U.S. Pat. No. 11,432,999, which is a National Stage of PCT/US2019/021494, filed Mar. 8, 2019, which claims the benefit of U.S. Provisional Application No. 62/658,028 filed Apr. 16, 2018. The aforementioned applications are incorporated herein in their entirety by reference.

TECHNICAL FIELD

This disclosure relates generally to pill dispensing systems, as well as methods for controlling and using such systems.

BACKGROUND

Pill separation, sorting, holding, and dispensing systems come in a variety of different forms for different uses. For example, blister packs, 7-day pill organizers, pill counters, and automatic pill dispensers for home or pharmacy use are widely commercially available. Each of these systems is suited for a particular type of use and level of complexity.

For example, a blister pack can maintain a hermetic seal around a medication and some blister pack packaging can be used to indicate the appropriate time and quantity of that pill to be taken. Blister packs are typically not suitable for dispensing different medications on the same day or variable amounts of types of medications that change over time, since the labeling for a blister pack is typically not customizable for an individual. Blister packs are also not reusable, as by their nature they are destroyed on first use.

Pill organizers come in a variety of sizes and shapes, but the most typical example is a 7-day pill organizer. In a pill organization system, the medications for a particular set of time (e.g., one week) can be pre-loaded into the organizer such that each day the consumer can simply open the organizer segment associated with the day and be assured that he or she is taking the correct medication. Pill organizers, however, typically start on a given day of the week (e.g., Sunday) and so if they are loaded on a different day (e.g., Tuesday) then the organizer will only be accurate for the remaining days of that week (e.g., Wednesday through Saturday). Furthermore, pill organizers can pop open or be improperly loaded, and rely upon the person taking the medication to know what the day is, to remember to open the associated organizer section, and to take each medication within that section at the appropriate time of day.

Automatic pill dispensers have recently begun to be commercially available. Typically, an automatic pill dispenser is a tabletop device that dispenses a medication or medications at a particular time and date. Automatic pill dispensers can be pre-loaded by health care professionals or by the patients themselves. Automatic pill dispensers tend to be bulky, difficult to load or reload, and cannot be moved easily if the patient is traveling, due to their mechanical complexity, size, and power requirements. Many patients who take pills regularly cannot rely on an automatic pill dispenser because, by nature of the medical conditions they suffer from, travel may be required regularly between the patient's home and a clinic, hospital, or other locations.

Thus, some patients will rely upon a combination of blister packs, pill organizers, and automatic pill dispensers, which can be confusing and require significant attention and planning to avoid taking too many or too few medications. Furthermore, health care providers, family members, and other caretakers may not be able to accurately monitor the quantity of pills or the time at which those medications are taken to ensure compliance with critical drug dose recommendations.

SUMMARY

Various embodiments described herein include devices that resolve the aforementioned problems with conventional pill dispensing systems. The systems and methods described herein include automatic pill dispensers that release pills in a trackable way and on a desired schedule, can be loaded at any day or time of day, can operate for significant periods of time away from power, are configured to travel well, and facilitate tracking and monitoring of pill consumption compliance for family members, caretakers, and health care professionals.

BRIEF DESCRIPTION OF THE DRAWINGS

Subject matter hereof may be more completely understood in consideration of the following detailed description of various embodiments in connection with the accompanying figures, in which:

FIG. 6D is a set of graphical user interface indications corresponding to filling an automatic pill dispenser according to an embodiment.

FIGS. 11-16 are Graphical User Interfaces according to various embodiments.

Figure 1A:
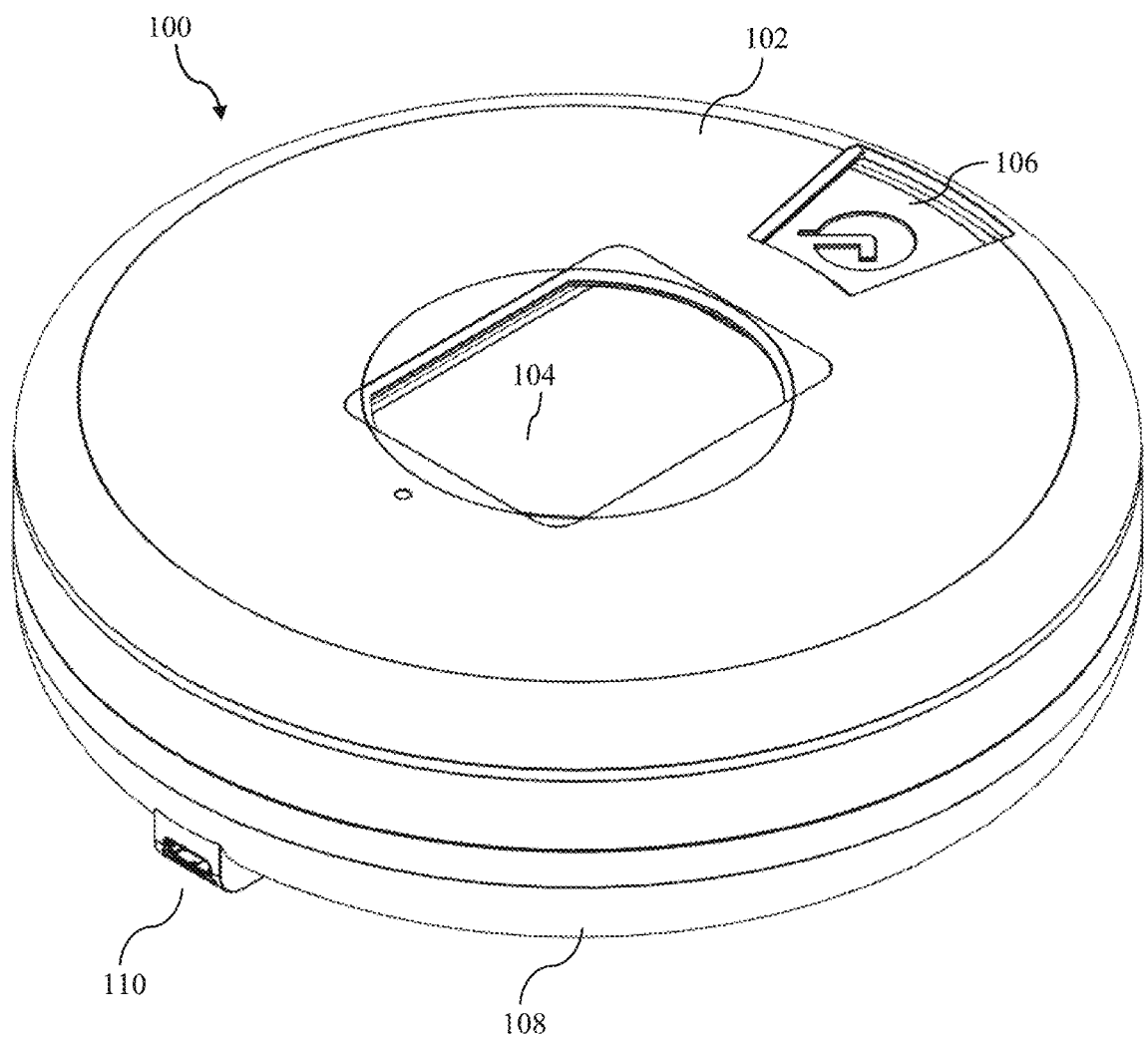
FIGS. 1A-1H depict an automatic pill dispenser according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

As described herein, an automatic pill dispenser can be used in multiple locations, and will adjust to being loaded or reloaded at any time, rather than permitting reloading only at specific times. The embodiments described herein monitor compliance with medication regimens more accurately than conventional dispensers, in that the removal of the medication from the dispenser can be monitored. As described in more detail below, the systems and methods described herein are designed with a consumer or patient in mind who may be traveling or moving from place to place throughout a medication regimen.

FIGS. 1A-1H depict a medication dispensing system 100, according to an embodiment.

FIG. 1A is a perspective view of the medication dispensing system 100. As shown in FIG. 1A, medication dispensing system 100 includes a lid 102, a screen 104, a zero position indicator 106, a base 108, and a charging port 110.

Lid 102 and base 108 combine to substantially enclose any medications and other components within medication dispensing system 100. However, there are two apertures within lid 102 that provide access to the inside of the medication dispensing system 100. First, screen 104 is accessible through an aperture in lid 102. Second, zero position indicator 106 is typically accessible through a second aperture defined by the lid 102. As described in more detail below, during use the aperture in lid 102 may not be positioned adjacent to zero position indicator 106.

Furthermore, base 108 includes a charging port 110 that facilitates charging or recharging a battery (not shown) within the medication dispensing system 100, or can be used for running medication dispensing system 100 on line voltage rather than on battery power. Charging port 100 can be used to transfer data, in embodiments, as well as providing electrical power.

Figure 1B:
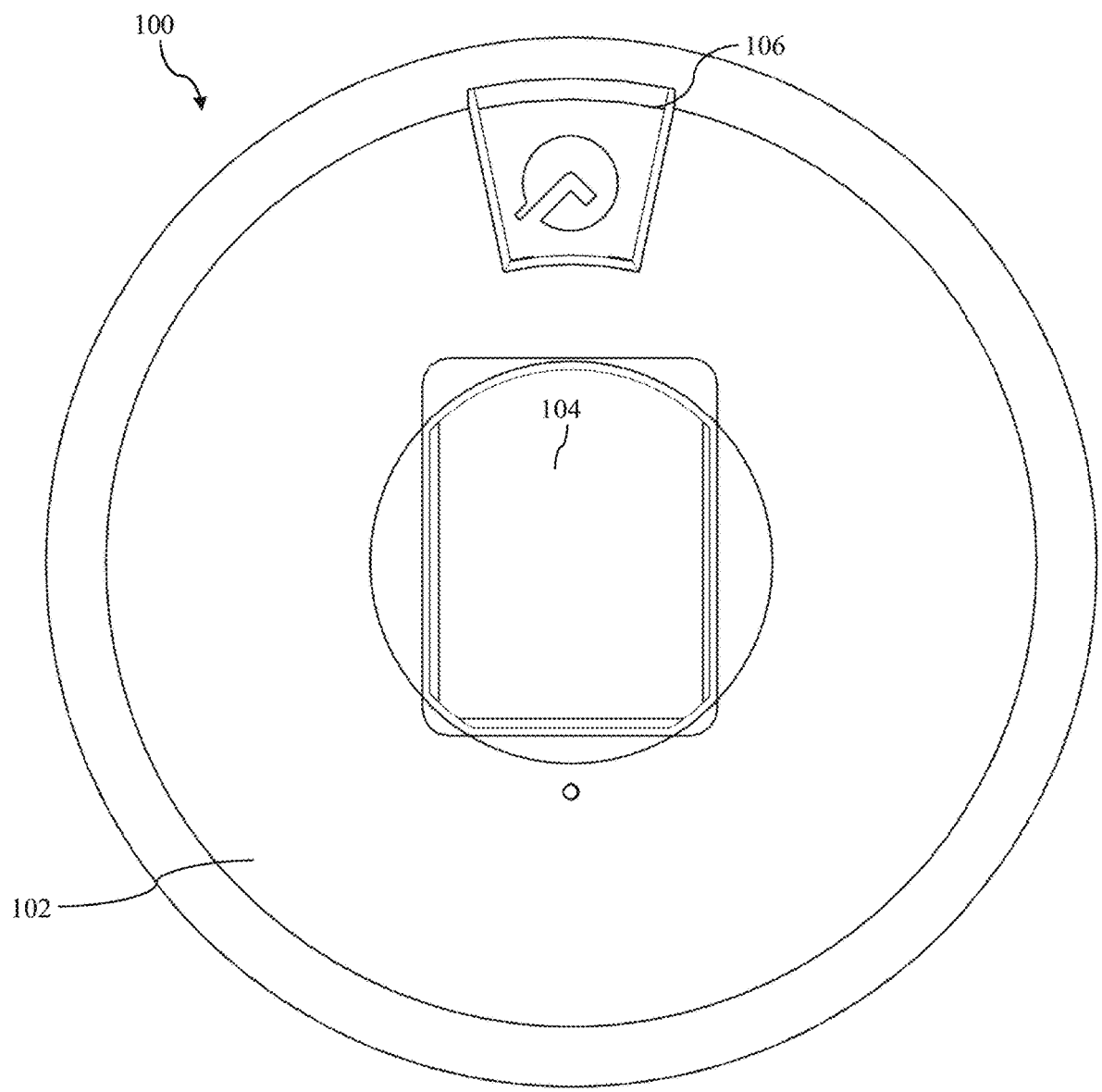
Figure 1C:
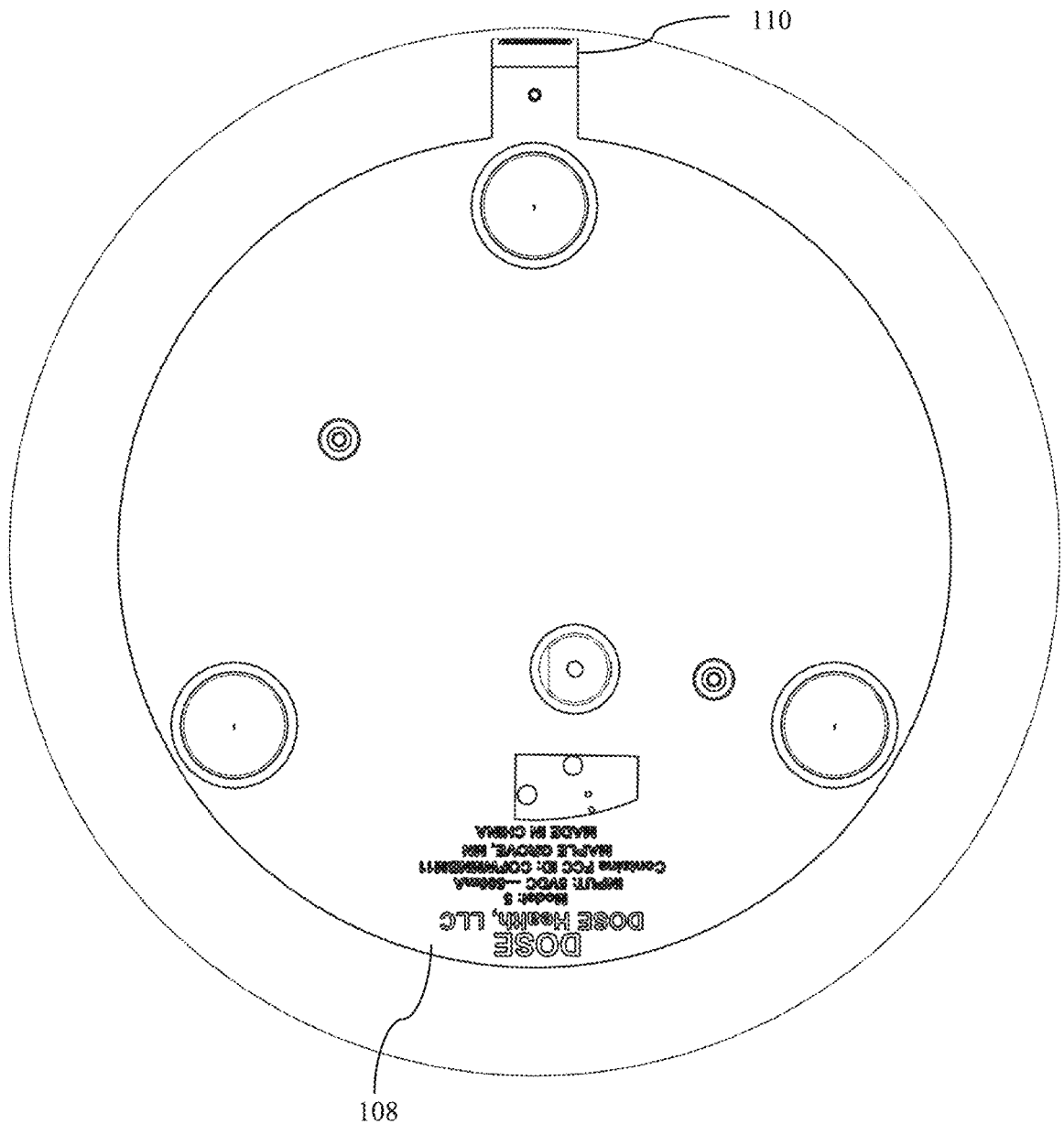
Figure 1D:
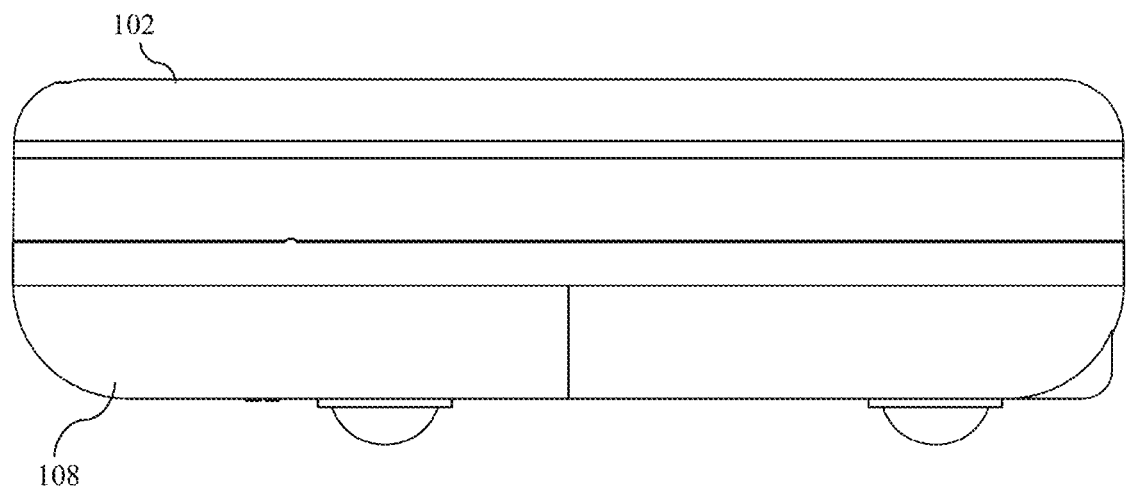
Figure 1E:
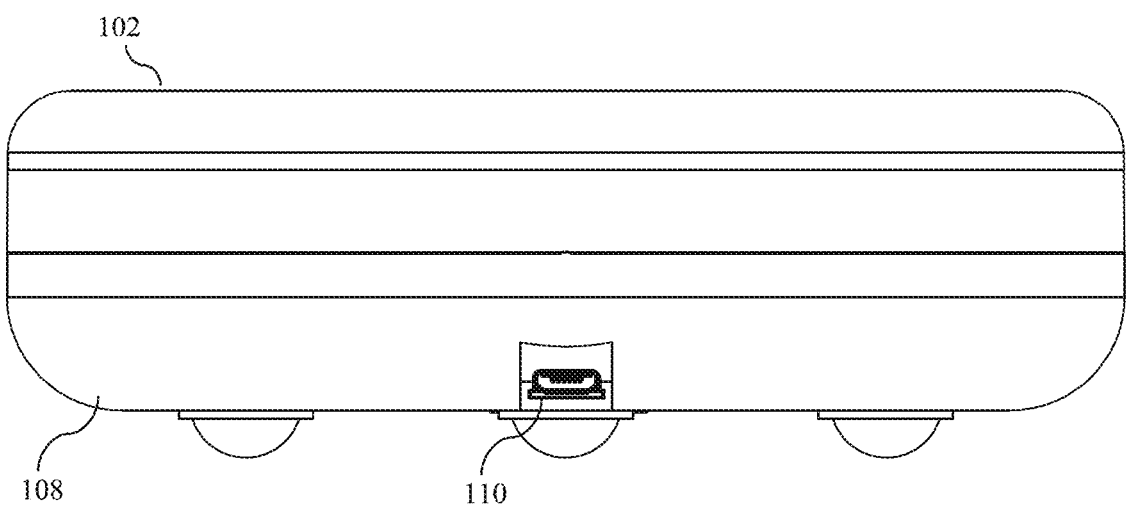

FIG. 1B is a top view of medication dispensing system 100, and FIG. 1C is a bottom view of the medication dispensing system 100. FIGS. 1D and 1E are side views of the medication dispensing system 100. It should be understood that some of the features depicted herein are not necessary for the operation of the device, and various alternatives could be used in other embodiments. For example, while FIG. 1B shows zero position indicator 106 with a checkmark-style indicator, in other embodiments other indicators could be used or, in some embodiments, no indicator need be present whatsoever. Likewise, while FIG. 1C shows a base 108 that includes several protrusions or feet, in alternative embodiments these feet or protrusions could be arranged, shaped, or sized differently, or could be absent altogether.

In FIGS. 1A and 1B, screen 104 is shown as having a rectangular shape. There are advantages to different shapes of screens, and a rectangular shape can be advantageous in that it provides an up-and-down orientation for a user. In other embodiments, there could be an advantage to, for example, a circular screen that would more accurately resemble the circular aperture of lid 102, to maximize screen size, for example.

Figure 1F:
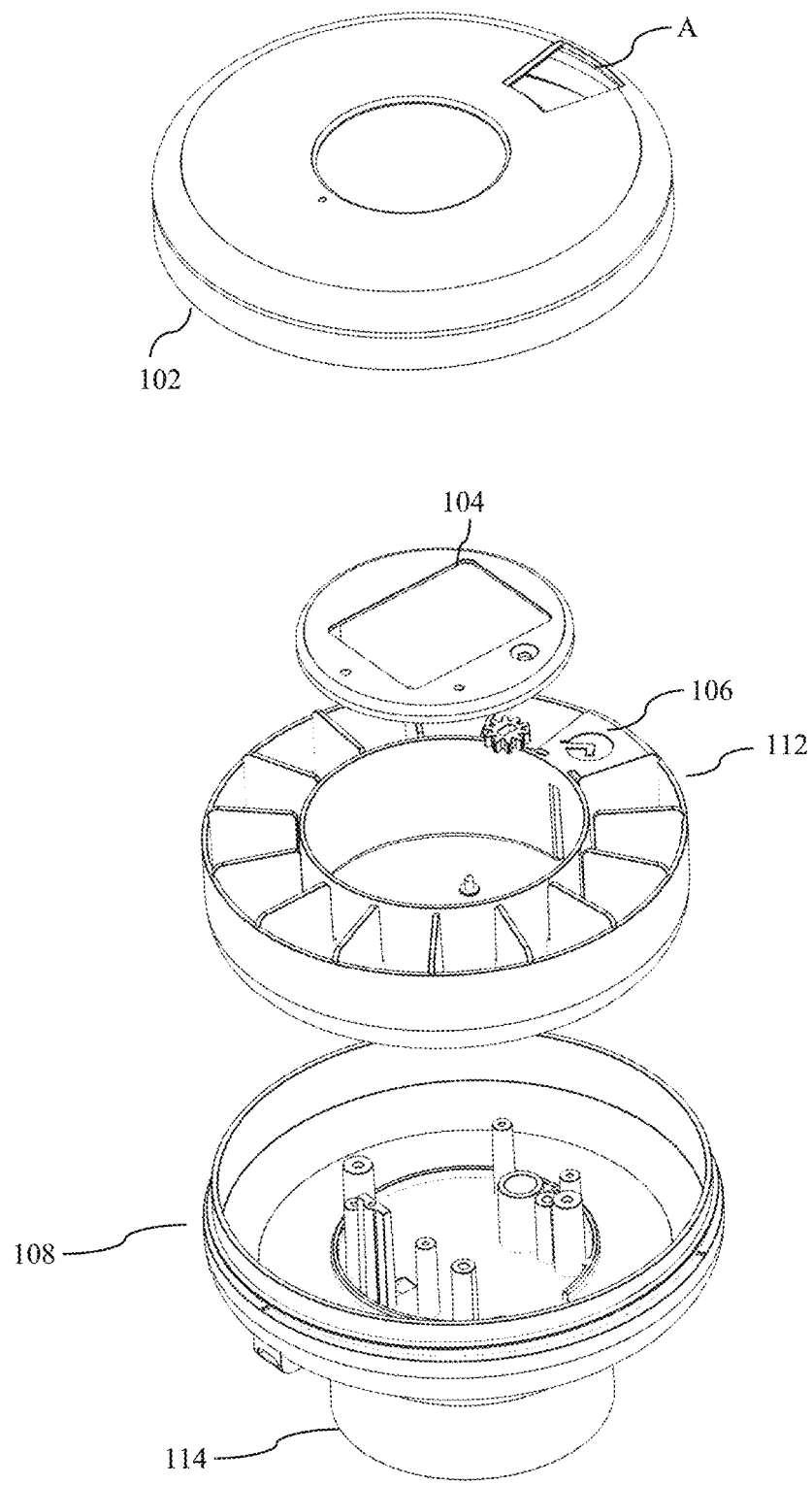

FIG. 1F is an exploded view of medication dispensing system 100. As shown in FIG. 1F, lid 102 and base 108 house several components therebetween, such as screen 104 and also including carousel 112 and motor 114.

Figure 1G:
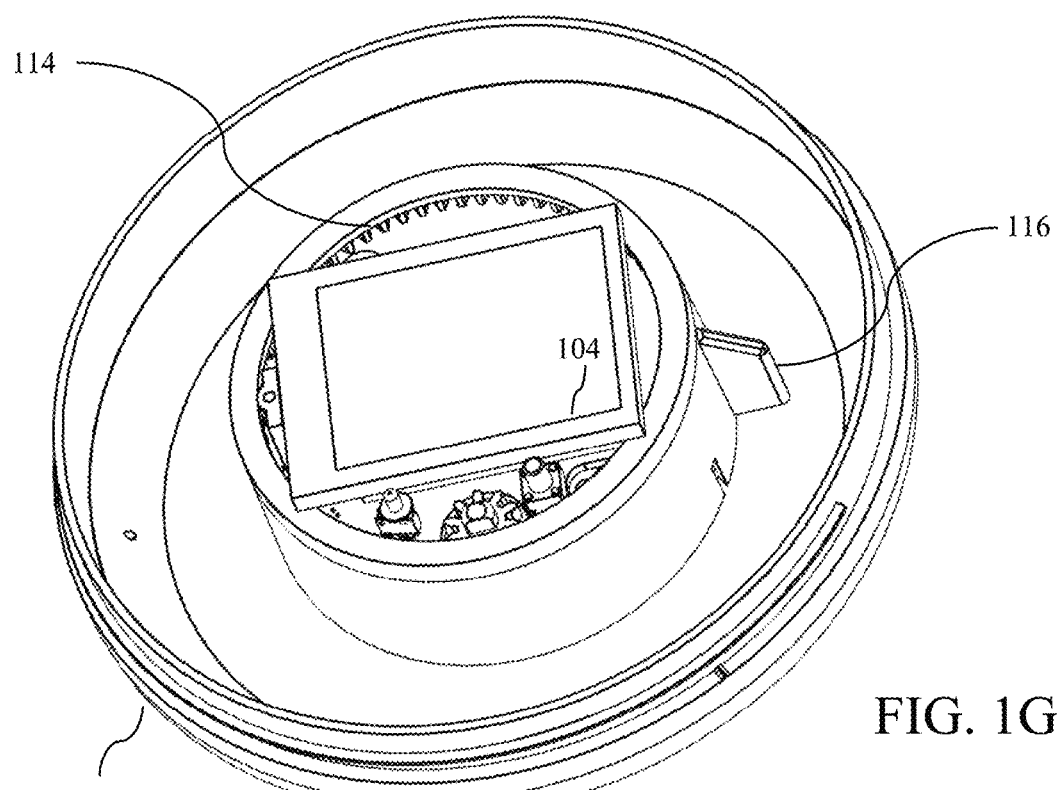
Figure 1H:
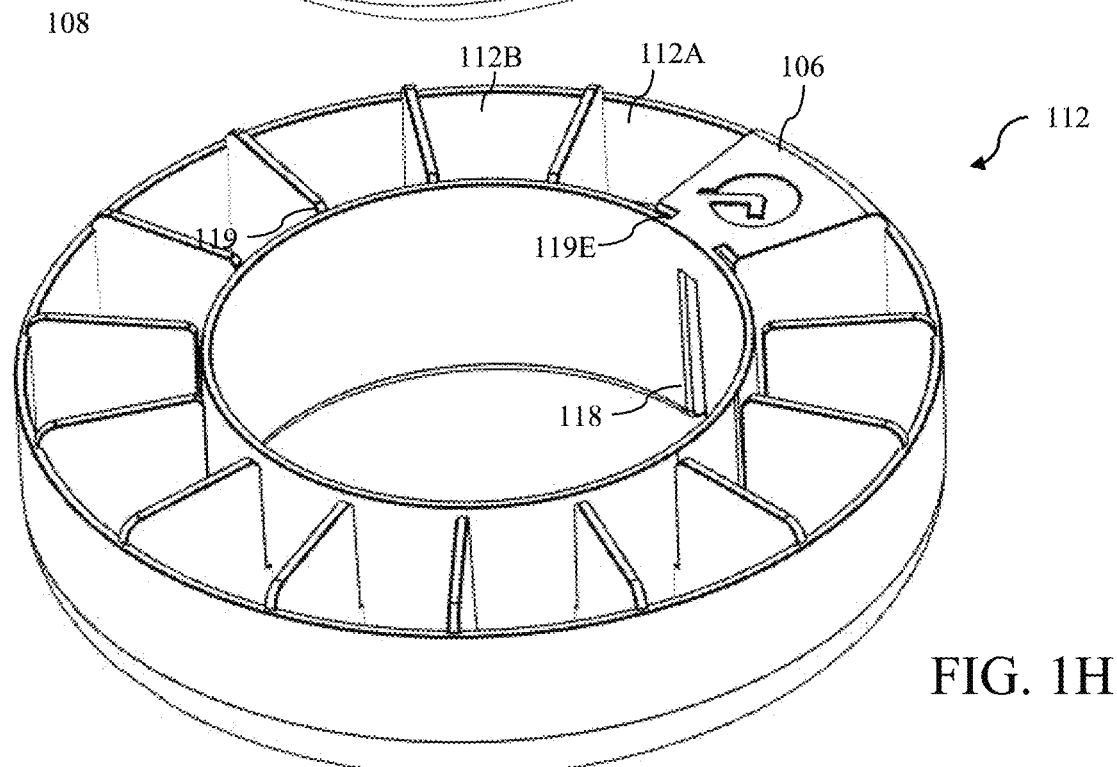

Carousel 112 and motor 114 are configured to engage with one another as illustrated by the partial perspective views thereof in FIGS. 1H and 1G, respectively. In particular, motor 114 includes a tooth 116 and carousel 112 includes a slot 118. Tooth 116 and slot 118 are configured to engage with one another and interlock, such that rotation of motor 114 causes a corresponding movement of tooth 116 relative to base 108 and thus a corresponding movement of carousel 112 relative to base 108. As shown in FIG. 1F, base 108 and lid 102 are engaged with one another to prevent relative rotation therebetween during use (in this embodiment, via a threaded connection) and therefore rotation of motor 114 causes movement of carousel 112 relative to the apertures therein. Accordingly, motor 114 can be engaged to rotate the carousel 112 such that any of the plurality of bins 112A, 112B, etc. are positioned adjacent to the aperture A in the lid 102. The bins 112A, 112B, etc., each have a size corresponding to that of the aperture A. In particular, the aperture A has a size corresponding to the top of each of the bins. In embodiments, the aperture A can have a different size or shape corresponding to the bins 112A, 112B, etc., to facilitate removal of pills from each bin 112A, 112B, etc., when the aperture A is moved adjacent to each one.

FIG. 1H further depicts a gap 119 between the walls of each bin and the center of the carousel. The gap 119 can be used to house an indicator strip, as described in more detail below. The gap 119 is present for each of the bins of carousel 112, and zero position indicator 106 includes gap ends 119E to set the position of the indicator strip.

Figure 2:
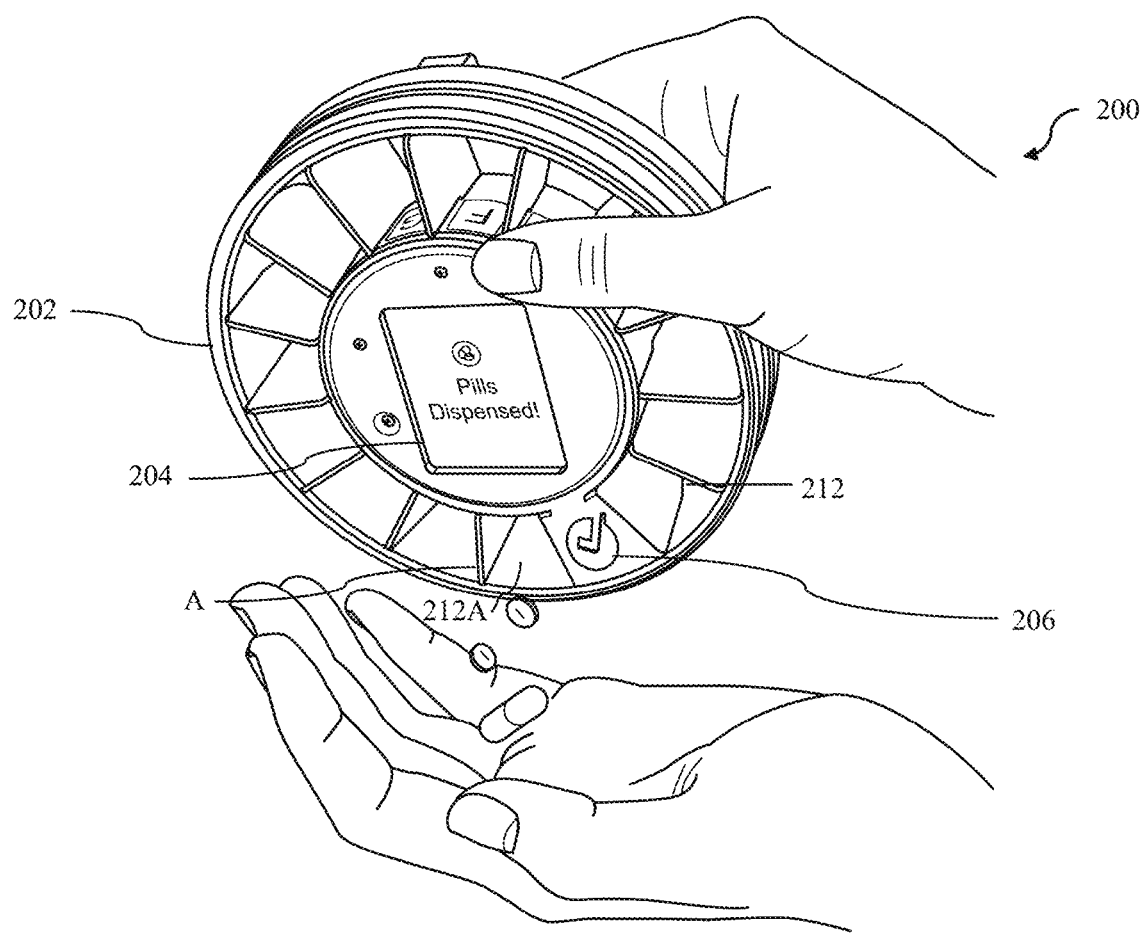
FIG. 2 is a perspective view of the automatic pill dispenser of FIG. 1 in use.

FIG. 2 depicts a medication dispensing system 200 in use. As shown in FIG. 2, medication dispensing system 200 includes a clear lid 202, a screen 204, and a zero position indicator 206, similar to the counterpart components of the device shown in FIGS. 1A-1H. In the stage of use shown in FIG. 2, medication dispensing system 200 has been activated to rotate a motor (not shown) such that the carousel 212 is positioned with first bin 212A adjacent to aperture A in lid 202.

Screen 204 of FIG. 2 shows an indicator that pills have been dispensed. In embodiments, the devices described herein can include sensors to detect the orientation, or change in orientation, of such devices relative to a gravitational field, or based on the use of accelerometers or other sensors to detect motion or rotation. When the device 200 is operated to expose any chamber of carousel 212 (e.g., chamber 212A) via aperture A, and the device 200 is subsequently rotated to cause the contents of that chamber 212A to fall out, then medication dispensing system 200 can indicate that the medication has been successfully dispensed. This indication can be on screen 204, at a remote location as described in more detail below, or both.

Figure 3A:
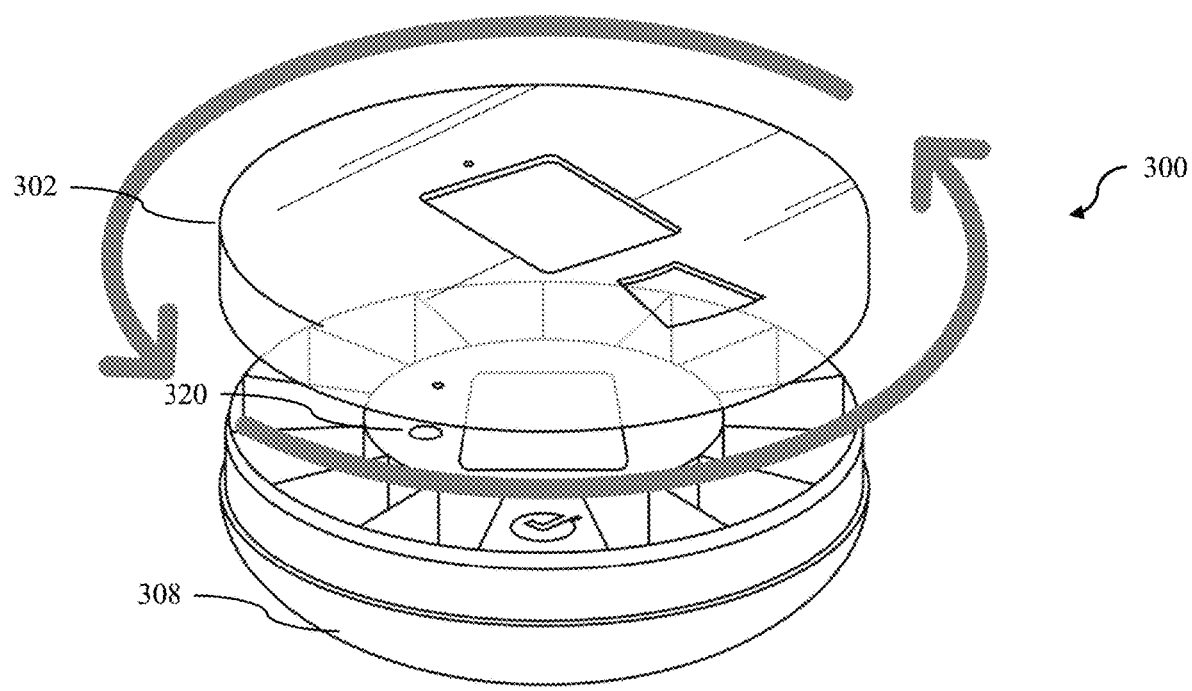
FIG. 3A is a partially exploded view of the automatic pill dispenser of FIG. 1, depicting removal of the cover.

FIG. 3A depicts removal of a lid 302 from a base 308 according to an embodiment, as indicated by the arrows showing rotation in a counter-clockwise direction. Button 320 detects whether lid 302 is engaged to base 308. In particular, when lid 302 is screwed completely on to base 308, button 320 is completely depressed. In contrast, when lid 302 is unscrewed from base 308, button 320 can pop out, which can in turn provide feedback to computerized components (not shown) within the device 300 that the lid 302 has been removed. This information can be used to operate the device 300, for example by indicating when the device 300 is being refilled, as described in more detail below.

Figure 3B:
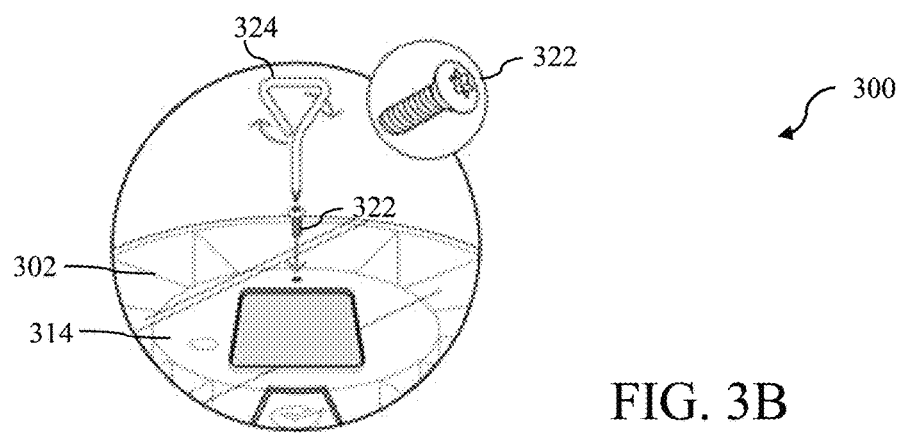
FIG. 3B is a partial view of the automatic pill dispenser of FIG. 1, depicting a safety mechanism for prevention of removal of the cover as shown in FIG. 3A.

FIG. 3B shows an optional locking feature of the device 300 of FIG. 3A. In particular, a kit or system that includes device 300 can include a screw 322 and a driver 324 that are configured to engage with one another. As shown in FIG. 3B, screw 322 can be driven through lid 302 and into motor housing 314 to prevent relative movement between base 308 and lid 302.

Screw 322 is shown in an inset of FIG. 3B to depict a unique head, such that only a particular driver 324 can be used to rotate it. In this way, lid 302 can be locked to prevent access to medications within device 300 by children, pets, or others who desirably cannot open the device 300.

Figure 4:
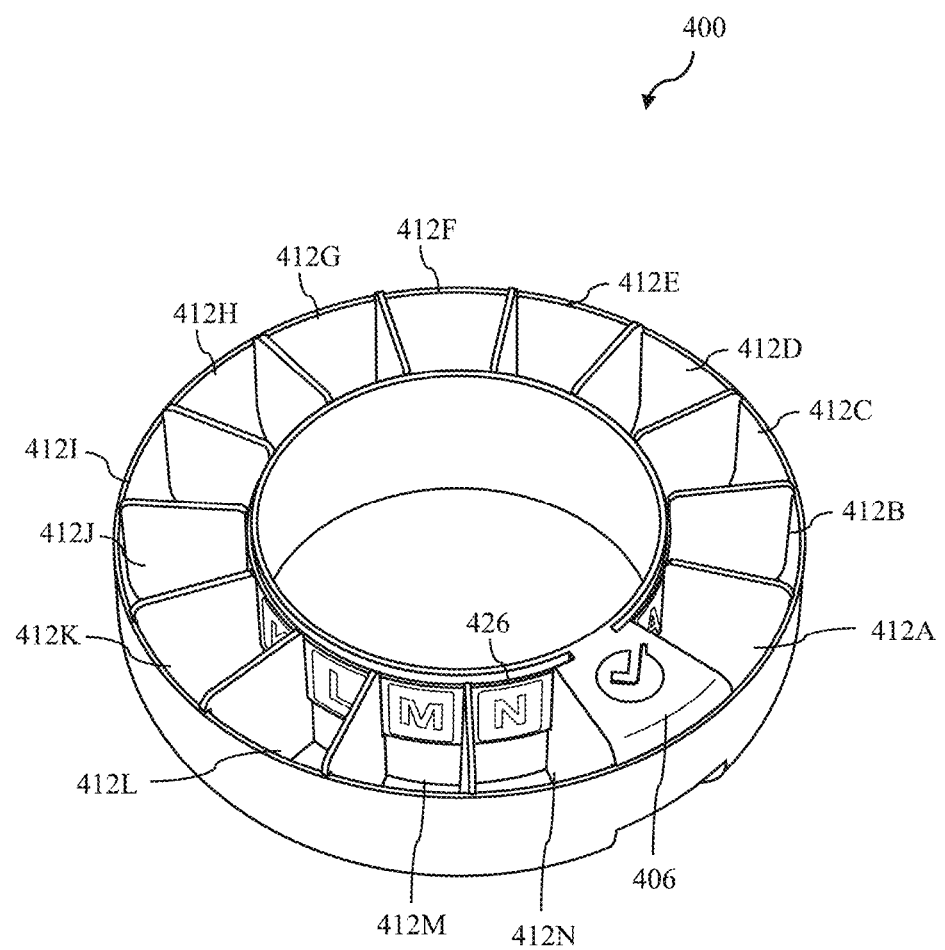
FIG. 4 depicts a carousel for an automatic pill dispenser, according to an embodiment.

FIG. 4 is a perspective view of a carousel 400 having a plurality of bins 412A-412N. Between the first bin (412A) and the last bin (412N) is a zero position indicator 406, similar to those described above with respect to the embodiments of FIGS. 1A-1H and 2. FIG. 4 further depicts indicator strip 426.

As shown in FIG. 4, indicator strip 426 includes a letter indicator corresponding to the associated bins 412A-412N. That is, the portion of indicator strip 426 adjacent to the first bin 412A includes an indicator "A" while the portion of indicator strip 426B adjacent to the second bin 412B includes an indicator "B" and so on, through the final (fourteenth) bin 412N which is adjacent to the portion of indicator strip 426 that says "N." As described in more detail below, the use of indicator strip 426 is helpful to a caretaker or a patient in filling or refilling the carousel 400.

In the embodiment shown in FIG. 4, the colors associated with each bin (412A-412N) vary. In particular, every other indicator of indicator strip 426 is orange, and the interdigitated indicators of indicator strip 426 are purple. The embodiment shown in FIG. 4 is therefore quite useful for a patient who is taking one medication by day (orange) and one medication by night (purple) every 24 hours. In alternative embodiments, different color schemes could be used to indicate different times of day or days of the week, as described below in more detail with respect to FIGS. 8A and 8B.

Figure 5:
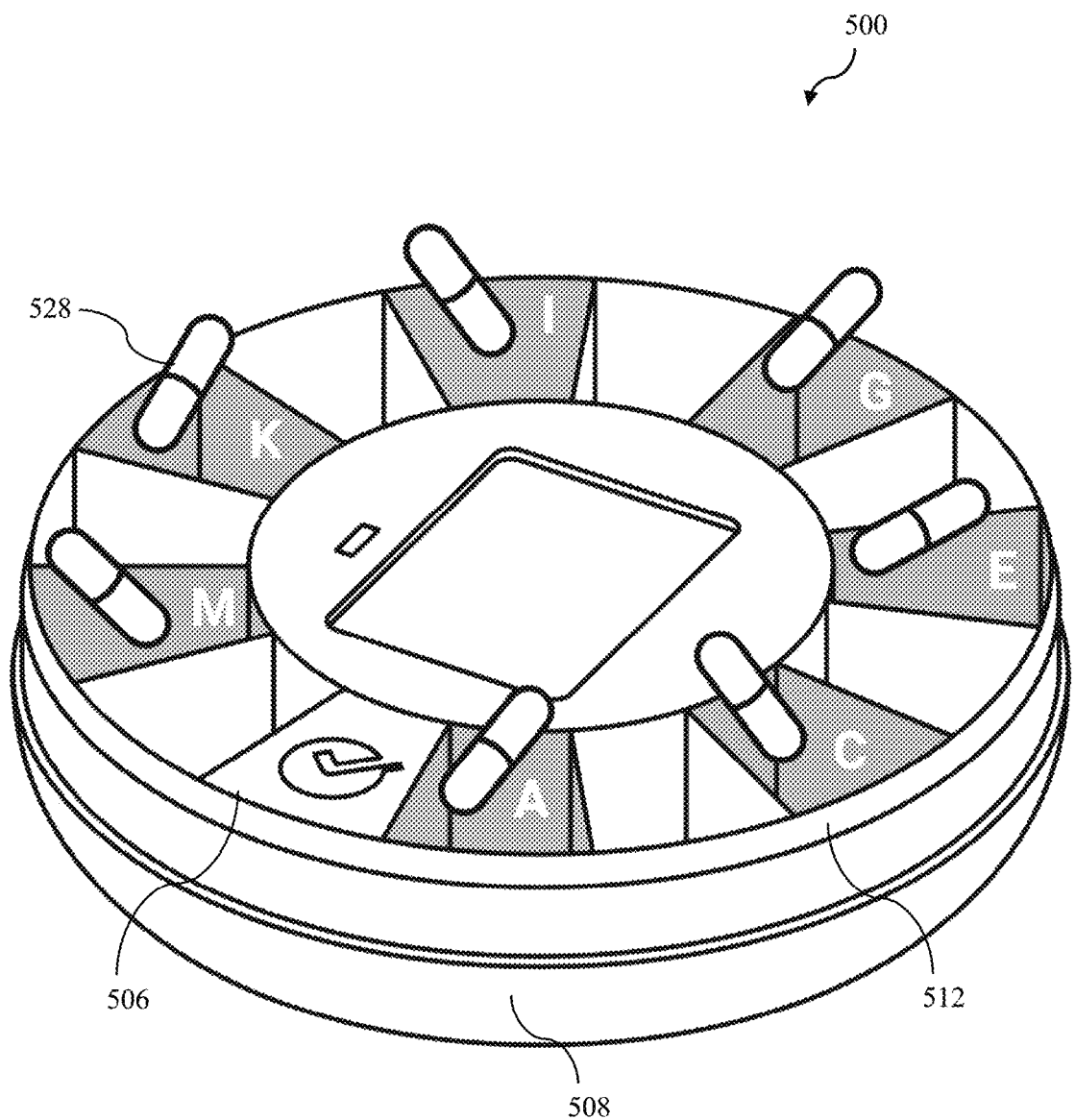
FIG. 5 is a schematic view of loading of an automatic pill dispenser, according to an embodiment.

FIG. 5 depicts a device 500 having a base 508 holding a carousel 512. The carousel 512 includes a zero position indicator 506 and a plurality of bins, half of which (A, C, E, G, I, K, and M) are associated with one of a plurality of pills 528. In the embodiment in which bins are associated with day and night medications described above for FIG. 4, pills 528 are to be taken each day. In use, various types and quantities of pills could be associated with each bin, and each bin can be sized appropriately to contain multiple medications or pill types and sizes.

Figure 6A:
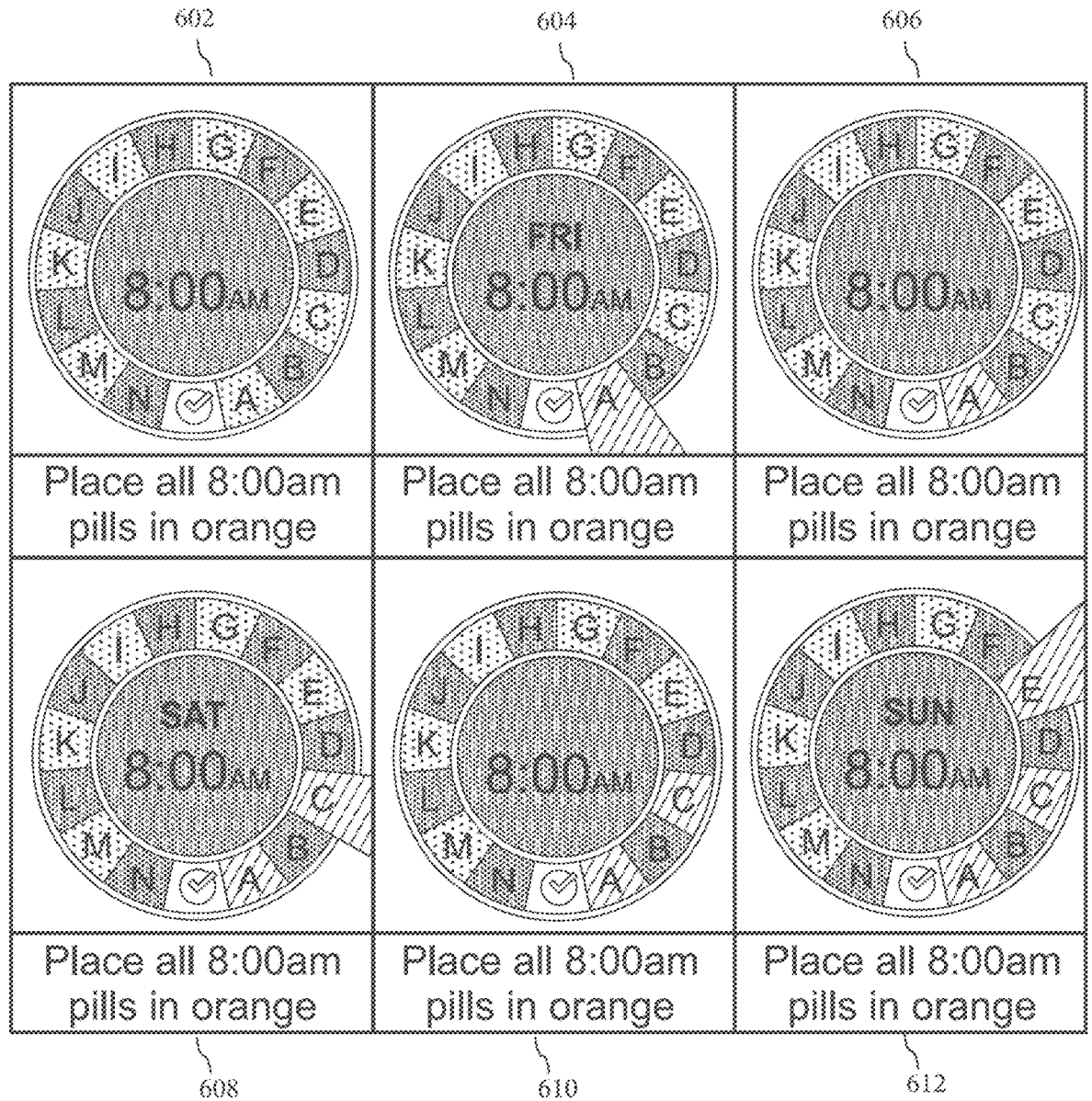
FIG. 6A is a set of graphical user interface indications corresponding to filling an automatic pill dispenser according to an embodiment.

FIG. 6A shows a plurality of graphical displays associated with the filling of a device as described with respect to the embodiments above. The stages shown in FIG. 6A can be a series of screens that are neither actionable prompts nor messages. Alternatively, in some embodiments a user could confirm the filling of each bin along with the prompts or messages.

Each lettered shape within the circle depicted in 602, 604, 606, 608, 610, and 612 references a lettered medication compartment within the tray. A block of color reaching from the letter to the outer edge of the screen indicates to the user which compartment to place their medications into by adjoining the lettered box to its lettered compartment counterpart. The block of color matches the color of the lettered block in the label strip (see FIGS. 4, 8A, and 8B). In this way, the user associates a color with a dispense time, aiding them in the filling process. To begin, the first medication set is placed into every other compartment, starting with compartment A, at 602. In the embodiment of FIG. 6A, the associated device is used to dispense twice daily, such that the "daytime" medication is loaded into alternating bins C and E (see 608 and 612). The user interface shown in FIG. 6A corresponds to the same bins that were filled as described in FIG. 5, above.

The filling process for the first set of medications continues until all bins associated with a first medication are filled. The compartments for the first set of medications remain orange to show the user which compartments they are to fill with their first set of medications. Next, the filling process for the second set of medications begins, as shown in FIG. 6B.

Figure 6B:
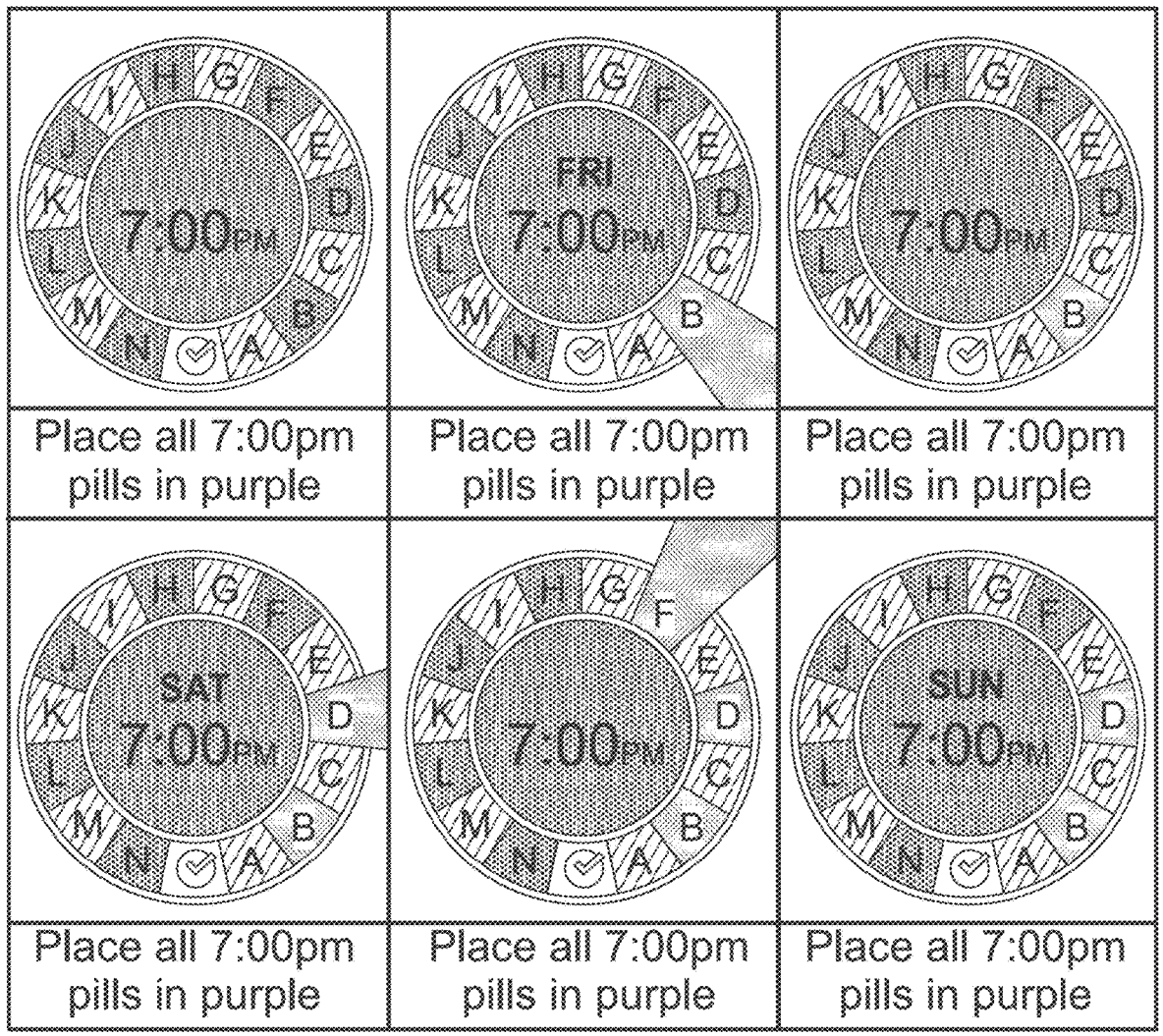
FIG. 6B is a set of graphical user interface indications corresponding to filling an automatic pill dispenser according to an embodiment.

Notably, the times associated with the dispensing of each of the first and second medications is displayed across the bottom of the graphical user interfaces depicted in FIGS. 6A and 6B. These times can be set by a user, and modified as needed. In embodiments, there could be only one dispense time per day, or there could be three or more dispense times per day. Furthermore, the medications taken each day may not be the same (e.g., a drug may be taken once a week, or once every three days). Such medication dispensing needs can be programmed in and the filling protocol adjusted accordingly so that the user will know exactly which pills to put in which bins pictorially.

Furthermore, while letters are used to indicate bins A-N in the embodiments described above, in alternative embodiments these could be pictograms, numbers, colors, or any other indicator that distinguishes bins from one another.

Figure 6C:
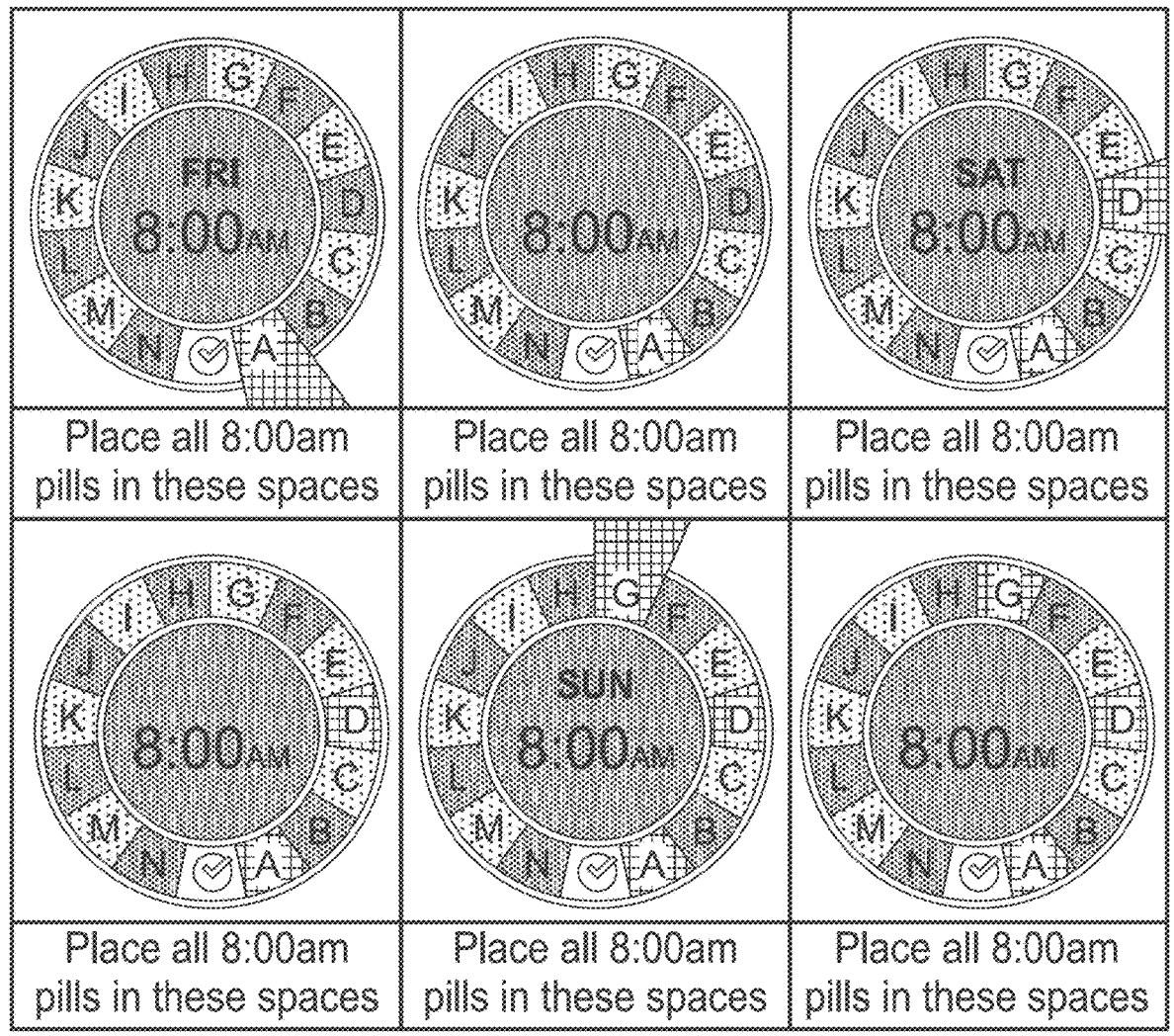
FIG. 6C is a set of graphical user interface indications corresponding to filling an automatic pill dispenser according to an embodiment.

FIGS. 6C and 6D depict GUIs for filling bins in predetermined medication regimens that correspond to three times a day dispensing and every day dispensing, respectively. As described above, various alternative predetermined medication regimes could be used, and as shown in FIGS. 6C and 6D a generic green background can be used for atypical dispensing regimes (or very simple regimes).

Figure 7:
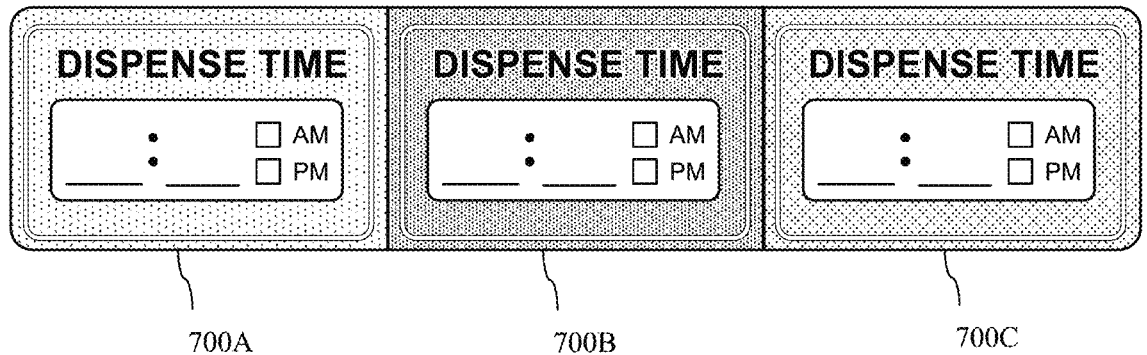
FIG. 7 is a label indicating pill dispensing times according to an embodiment.

FIG. 7 depicts three stickers 700A, 700B, and 700C, which can be used in coordination with the graphical user interfaces described in FIGS. 6A and 6B. Stickers 700A, 700B, and 700C are color-coordinated, in the embodiment shown in FIG. 7, and indicate the time at which the particular medications should be taken. In this way, in the event that an associated device runs out of power or is nonfunctional for any other reason, a user will know what time each bin of pills should be taken. Furthermore, in some embodiments carousels of pills may come pre-packaged and the carousels may be labeled with one or more of the stickers 700A-700C that indicate the proper times for consumption of those pills, so that a user will know what times to program a device that houses that carousel.

Figure 8A:
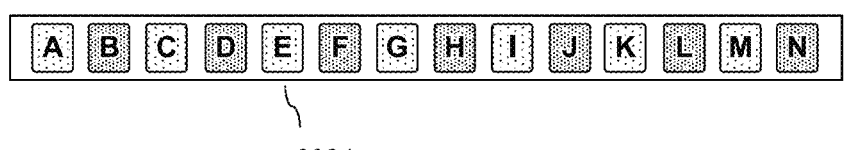
FIGS. 8A and 8B are guidance strips for loading pills into an automated pill dispenser according to an embodiment.
Figure 8B:
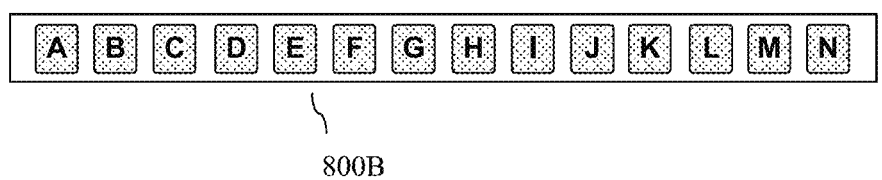

FIGS. 8A and 8B are plan views of indicator strips 800A and 800B, respectively. These indicator strips can be made of a strip of flexible material, or a rigid material having contours matching that of a corresponding slot of a carousel (see, e.g., FIG. 4). Each of the indicator strips 800A and 800B include lettering indicating the same range A-N to correspond to fourteen bins in a carousel. However, whereas indicator strip 800A of FIG. 8A includes alternating purple and orange lettering backgrounds, indicator strip 800B of FIG. 8B includes only green lettering backgrounds. Thus the indicator strip 800A may be more appropriate for alternating between two types of pills taken at different times of day (or pills taken once a day but on alternating days) whereas indicator strip 800B may be more appropriate for dispensing the same type and quantity of pills from each bin in a carousel.

Indicator strips 800A and 800B can be removable and separate from a carousel, such that as medication quantities or types changes, or as the medication dispensing schedule is modified by a doctor or pharmacist, different indicator strips can be swapped out as appropriate. Although only one-colored or two-colored strips are shown in FIGS. 8A and 8B, respectively, it should be understood that in alternative embodiments there could be three- or four-colored (or more) strips, and that they may not always be alternating but could instead be in other patterns. Furthermore, a person of skill in the art will recognize that while fourteen bins is a convenient number in many applications (since it provides two bins per day of the week), in some embodiments it may be more beneficial to have relatively more or fewer compartments. Fewer compartments results in the ability to store a larger number of pills in each bin (assuming the overall system stays the same size) while more compartments results in the ability to serve a patient for more dispensing rounds before refilling is required.

Figure 9:
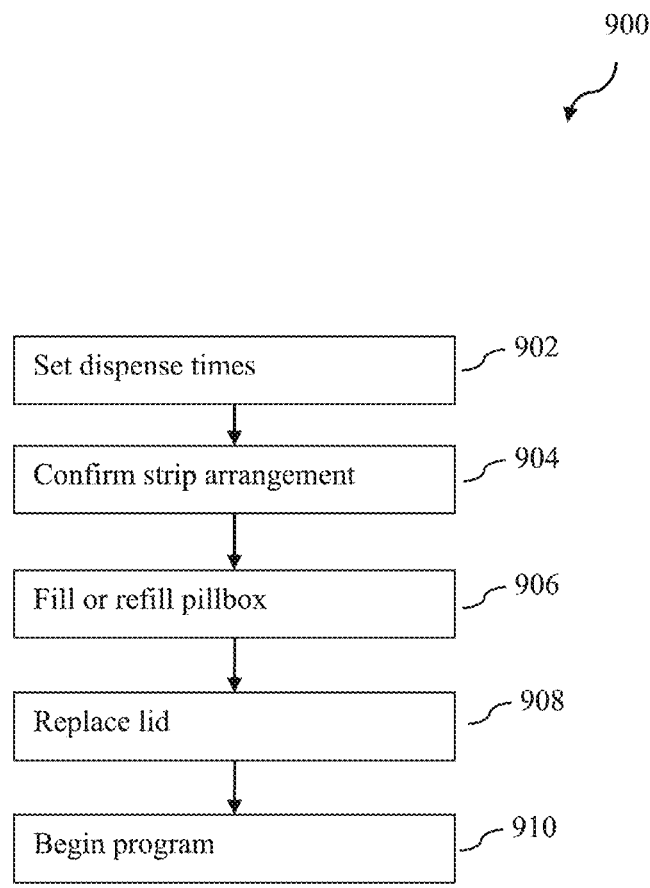
FIG. 9 is a flowchart of a method for loading an automated pill dispenser according to an embodiment.

FIG. 9 is a flowchart that depicts a method 900 for filling a device according to an embodiment.

At 902, dispense times are set. A user can be given options to adjust the number corresponding to the amount of times that medications will be dispensed from the pillbox per day either up or down (e.g., using the plus or minus icons), or to return to a previous screen, or to continue with the device's dispense setup process. The user can adjust the number of times per day as well as the particular dispensing times at 902. The user can set the device to dispense 1-4 times a day in one embodiment. Users who take medications 3 or more times per day may prefer to use two devices simultaneously, each dispensing medications twice a day (for 4 times a day dispensing), or once dispensing once a day and the other twice a day (for 3 times a day dispensing), etc. Both the dispense time setup process and the medication filling process are the same regardless of the number of times the user sets the device to dispense.

The user is then given the option to adjust the time for the first dispensing each day, or to return to the previous screen, or to continue with the device's dispense setup process. Setting the first dispense time can be followed by setting the second dispense time and any subsequent dispense times as needed.

At 904, the strip arrangement is confirmed. Confirming strip arrangement can include verifying the dispensing schedule that was entered at 902, as well as verifying that the proper color or indicator arrangement is visible on the indicator strip within an associated carousel. In embodiments, an image of the indicator strip can be displayed so that a user can verify that the correct one is present. Denying the correct strip arrangement or dispense times will take a user back to 902, allowing the user to reset the medication dispense times. Confirming that the medication dispense schedule is correct will finish the dispense time portion of the device's dispense setup process.

At 906, the pillbox is filled (or refilled). As shown in FIG. 3A, for example, the lid can be removed from the pillbox to permit access to the carousel and bins thereof, causing a sensor to detect that the lid has been removed and that the pillbox is open. In the embodiment shown in FIG. 3A the sensor is mechanical, though in alternative embodiments electronic sensors such as capacitive sensors, giant magnetoresistive sensors (GMRs), or completion of an electrical circuit between the lid and the housing, could be used to verify whether the lid is attached or detached from the base.

One embodiment of filling or refilling a pillbox is shown in FIGS. 6A and 6B, though as previously described with respect to the indicator strips of FIGS. 8A and 8B in alternative embodiments a variety of pill dispensing schedules will result in accompanying differences in the filling pattern.

At 908, the lid is replaced, and at 910 the program is begun. At each of 908 and 910, a user can confirm via the display touchscreen or other buttons that the task is complete.

Figure 10:
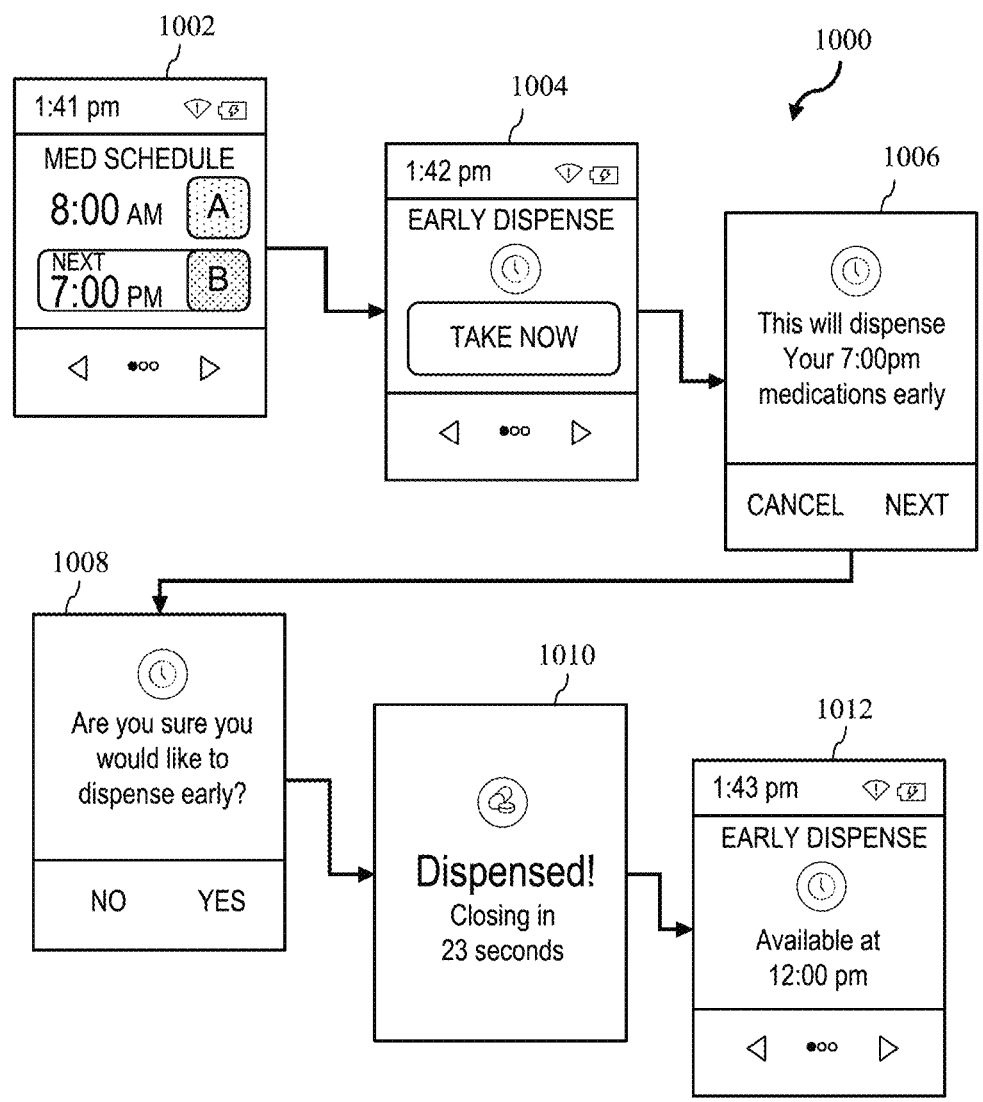
FIG. 10 is a flowchart of a method for early dispensing from an automatic pill dispenser according to an embodiment.

FIG. 10 is a flowchart depicting graphical user interfaces (GUIs) associated with an early dispense method 1000. Early dispensing may not be an option for all embodiments, but can be useful for patients whose schedules do not permit them to be available at an exact time due to travel or other commitments, for example.

At 1002, user is given two options, to either navigate right or left among the menu screens using, in this embodiment, the right or left arrows. In this embodiment, the dots along the bottom of the screen between the two arrows indicate the number of menus and the white dot indicates which screen is currently displayed in relation to the other menu screens.

At 1004, a user has selected one of the options on the screen at 1002 associated with early dispensing. At 1004, the user is given three options: the user can either navigate right or left among the menu screens using, in this embodiment, the arrows, or to dispense the next scheduled medication early by pressing TAKE NOW.

At 1006, the user has pressed TAKE NOW, an actionable prompt is displayed. The user is given two options: to either cancel their early dispense or proceed. In the method 1000, the user selects NEXT.

At 1008, a verification screen appears giving a user the option to either cancel their early dispense or proceed with dispensing their medications early. In the method 1000, the user selects YES.

At 1010, the lid of the device is rotated relative to the remainder thereof, so that an aperture therein is arranged above the next medication dispensing bin in the preprogrammed pill dispensing sequence. Various additional screens can be present between 1008 and 1010, such as a screen indicating that the aperture is being moved, or an instruction to flip the pillbox over to dispense. The method 1000 includes resetting the pillbox (i.e., moving the aperture back over the zero position indicator) after a preset amount of time. This timer resetting feature allows the user to have additional time if they are having difficulty with removing the medication from the compartment with the first flip.

At 1012, the early dispense feature is shown as locked out until a later time. After medications have been being dispensed early, the early dispense screen can display this message. The next available time is dependent on when the next medication is scheduled to be taken. This is a safety measure because many users need to take their medications at certain times of the day, and early dispensing twice could put a user at risk. It also prevents a confusing situation where an early dispense is possible for the next morning medication the night before, for example.

FIG. 11 depicts a series of GUIs associated with the Dose Anywhere method 1100. According to the Dose Anywhere method 1100, a user may use a device to couple the device to a wireless network and monitor or set medication schedules from anywhere.

At 1102, the user is given arrows to navigate right or left among the menu screens using, in this embodiment, the arrows, or to edit the medication schedule. In this embodiment, the dots along the bottom of the screen between the two arrows indicate the number of menus and the white dot indicates which screen the user is currently on in relation to the other menu screens. The second of these four screens is shown at 1104, corresponding to Dose Anywhere. In method 1100, the user selects the Dose Anywhere option at 1102, and the EDIT button at 1104.

At 1106, the user is given the option to connect to a network. At 1106, after selecting the START button, the device attempts to connect to WiFi, cellular, BLE, or any other connectivity option. If a connection is unsuccessful, or if the user selects the second screen rather than the START button at 1106, then the screen at 1108 appears prompting the user to either create an account or initiate a connection to a wireless network. 1110 depicts a prompt to a user to create an account if needed.

At 1112, a user is prompted to refill the pillbox under the Dose Anywhere method 1000. The user is given three options: To either navigate right or left among the menu screens using, the arrows, or to start the pillbox refill process. The Dose Anywhere refilling process is similar to those described above with respect to FIGS. 6A and 6B, for example.

Following setup of the Dose Anywhere method 1100, a device can connect wirelessly to communicate medication dispensing adherence to a medical professional, caregiver, or other interested person (such as family or to the user himself or herself).

FIG. 11 is an anonymized screenshot of a GUI that can be used to monitor adherence by, for example, a medical professional such as a doctor or pharmacist. The user will be greeted with the GUI shown in FIG. 11 when they open their Dose Dispense account. The GUI lists all of the devices associated with the user and gives a quick overview of the status of each compartment (red for missed compartments as indicated by compartments D and I on the first line associated with Name 1, for example, and green for dispensed compartments), the schedule, the connection status of the device, and their adherence rate. The user can click on the name of the pillbox to look at the details of that particular pillbox.

Figure 12:
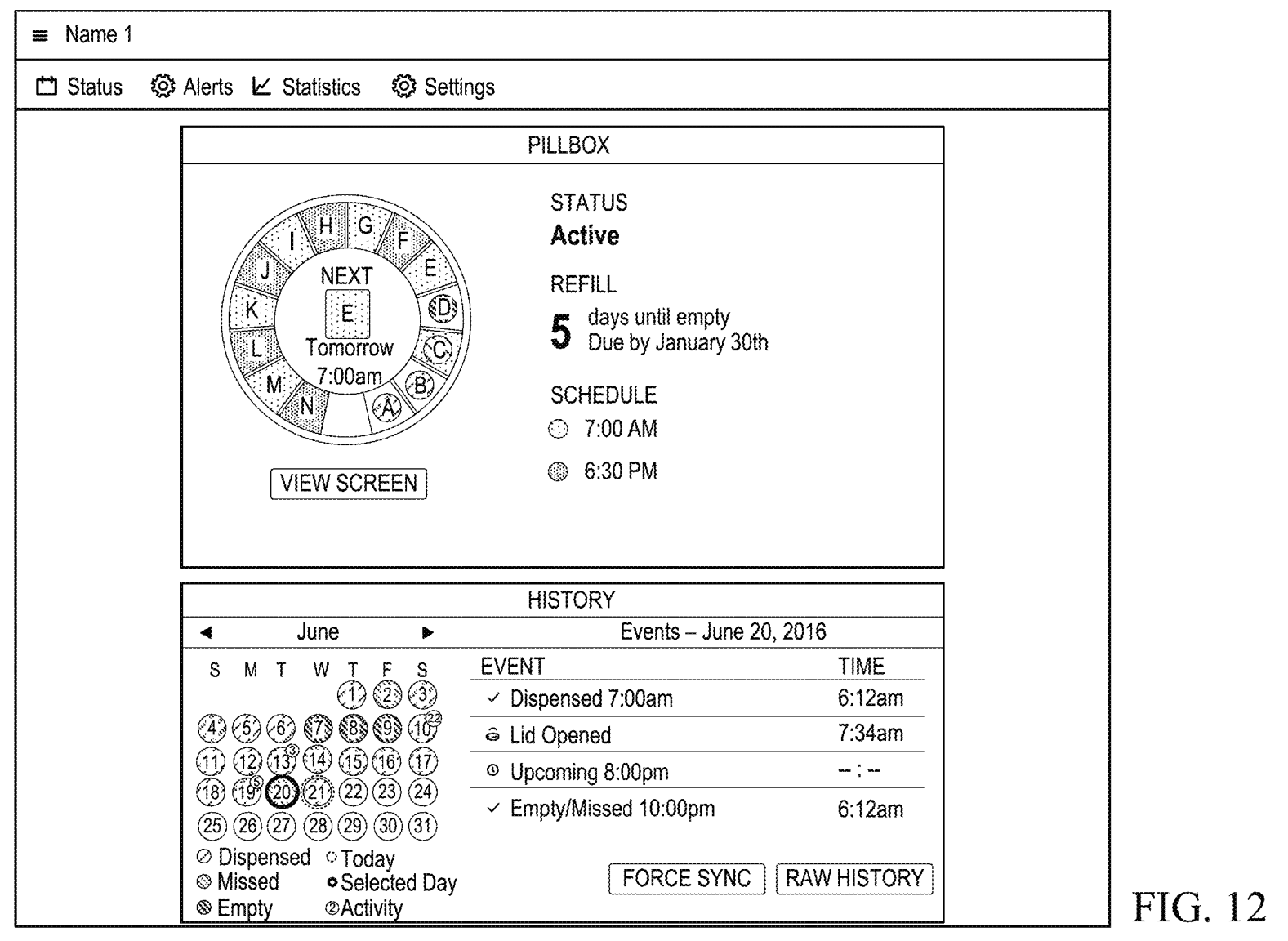

FIG. 12 shows several graphics that gives the user information on which medication is to be taken next and marks each previous compartment as either dispensed, missed, or early dispensed. Such information is located under the "Status" tab (i.e., the leftmost of the four tabs shown at the top of the GUI). The "Pillbox" window shows the pillbox with each compartment, color-coded to match the tray label, whether it's orange and purple for twice a day or green for once, thrice, or four times a day. In this example, the 7:00 AM medication is orange and the 6:30 PM medication is purple. Each compartment is marked as either dispensed or missed after the two-hour window to take the medication after the dispense time is up. The "History" window shows the pillbox's medication dispense history in the format of a monthly calendar. A color-coded key is provided, showing what each color that fills the circle representing each day stands for. "Dispensed" is green, "Missed" is orange, "Empty" is yellow, and the red notification icon shows an "event," such as the pillbox being unplugged or plugged in, flipped over, or it's lid unscrewed. The "events" are an important metric as oftentimes it is an indicator of the pillbox having been tampered with. The panel to the right of the calendar shows the events of a selected day, in this case being June 20th.

Figure 13:
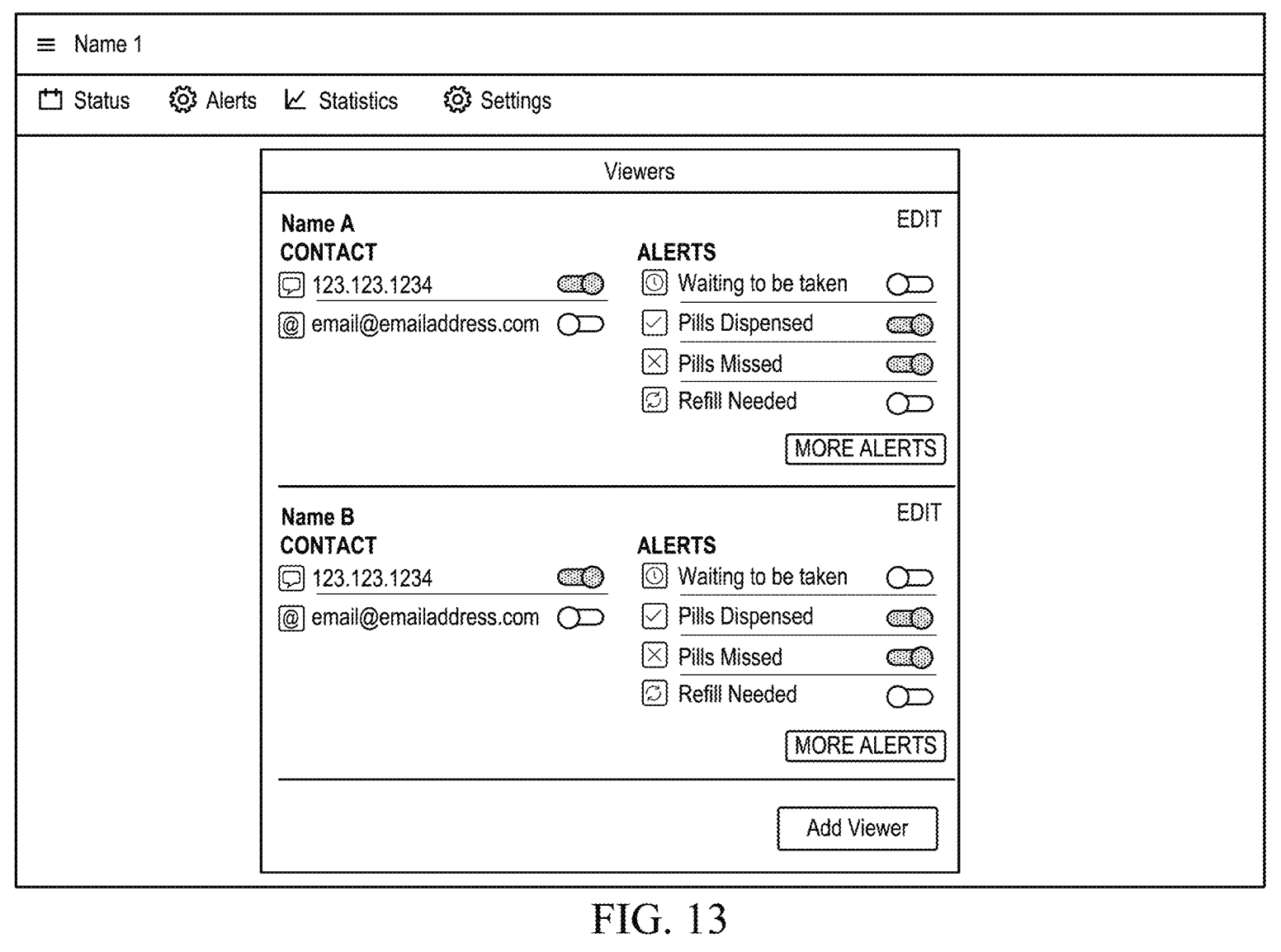

FIG. 13 displays dose dispense alert triggers for a viewer. In the embodiment shown in FIG. 13, a viewer ("Name 1") is able to receive alerts based on events that occur for two associated people ("Name A" and "Name B"). As shown by the toggled items in FIG. 13, Name 1 will receive phone calls when pills are dispensed or when pills are missed by either of Name A or Name B. The user Name 1 has decided not to receive notifications by email, nor to receive notifications when a refill is needed or when pills are waiting to be taken. In embodiments, pills can become accessible and the aperture remain associated with the corresponding bin for some period of time (e.g., 30 minutes) before the pills are considered "missed." Thus, Name 1 will not receive a notification if Name A or Name B take their pills within that window.

As shown in FIG. 13, different people who have different monitoring needs can customize the types of alerts that are received. A health care professional may, for example, wish to only know when a user misses taking his or her pills. A family member may wish to know all events, including when pills are dispensed on time. A pharmacist may wish to know only when a refill is needed. Multiple viewers can be given access to a single patient's pill dispense schedule so that the desired alerts are generated for each party.

Figure 14:
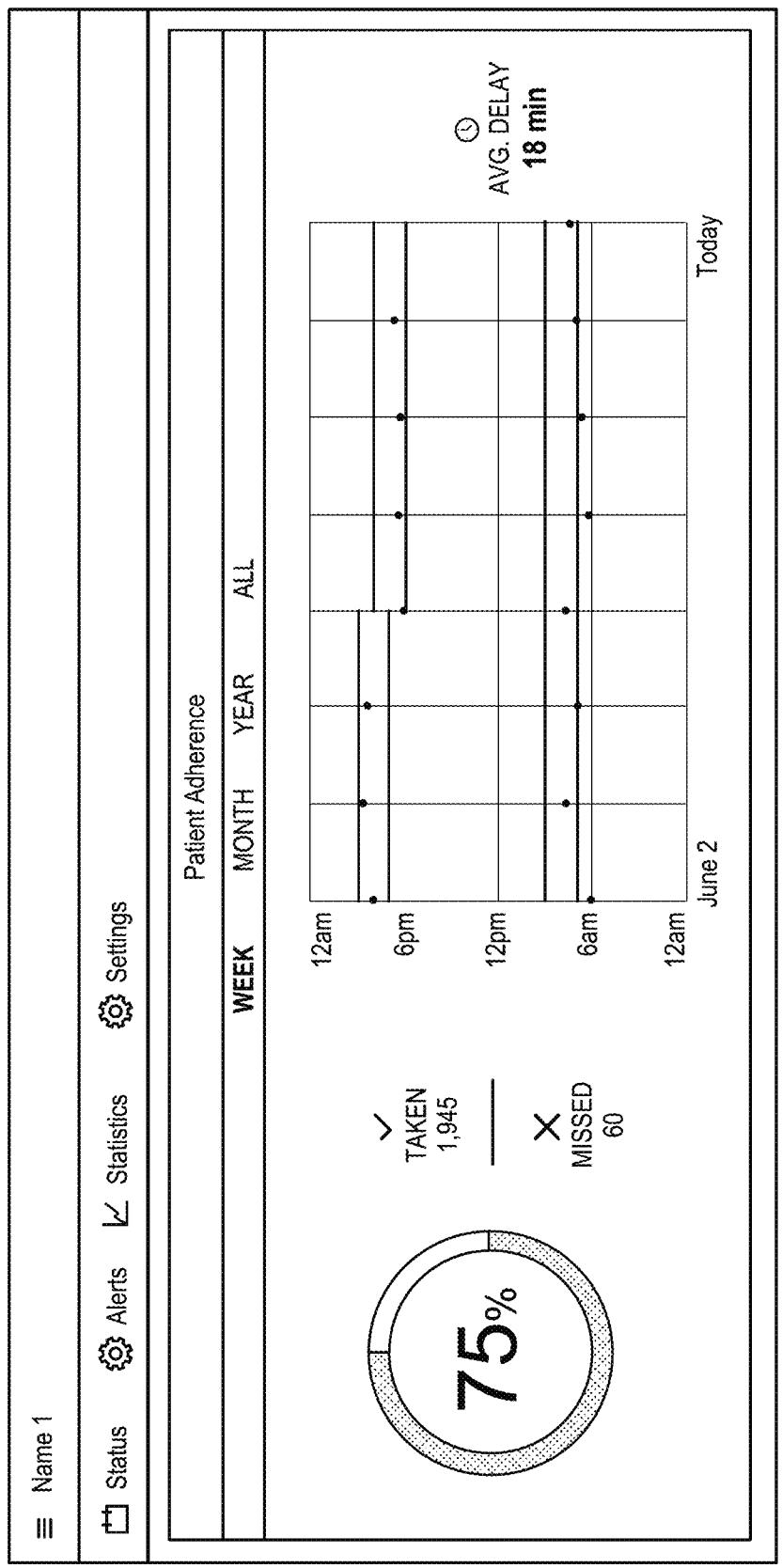

FIG. 14 shows statistics associated with a particular user ("Name 1") for adherence. The user is able to select which view they want, ranging from "WEEK" to "ALL." The graph includes an average delay metric, showing the user for how long on average medications were waiting to be taken after their scheduled dispense times. The orange lines indicate the two hour window in which medications can be taken after the set dispense time, after which, if the medications are missed, the pillbox with rotate closed and the medications in that compartment will be marked as missed.

Figure 15:
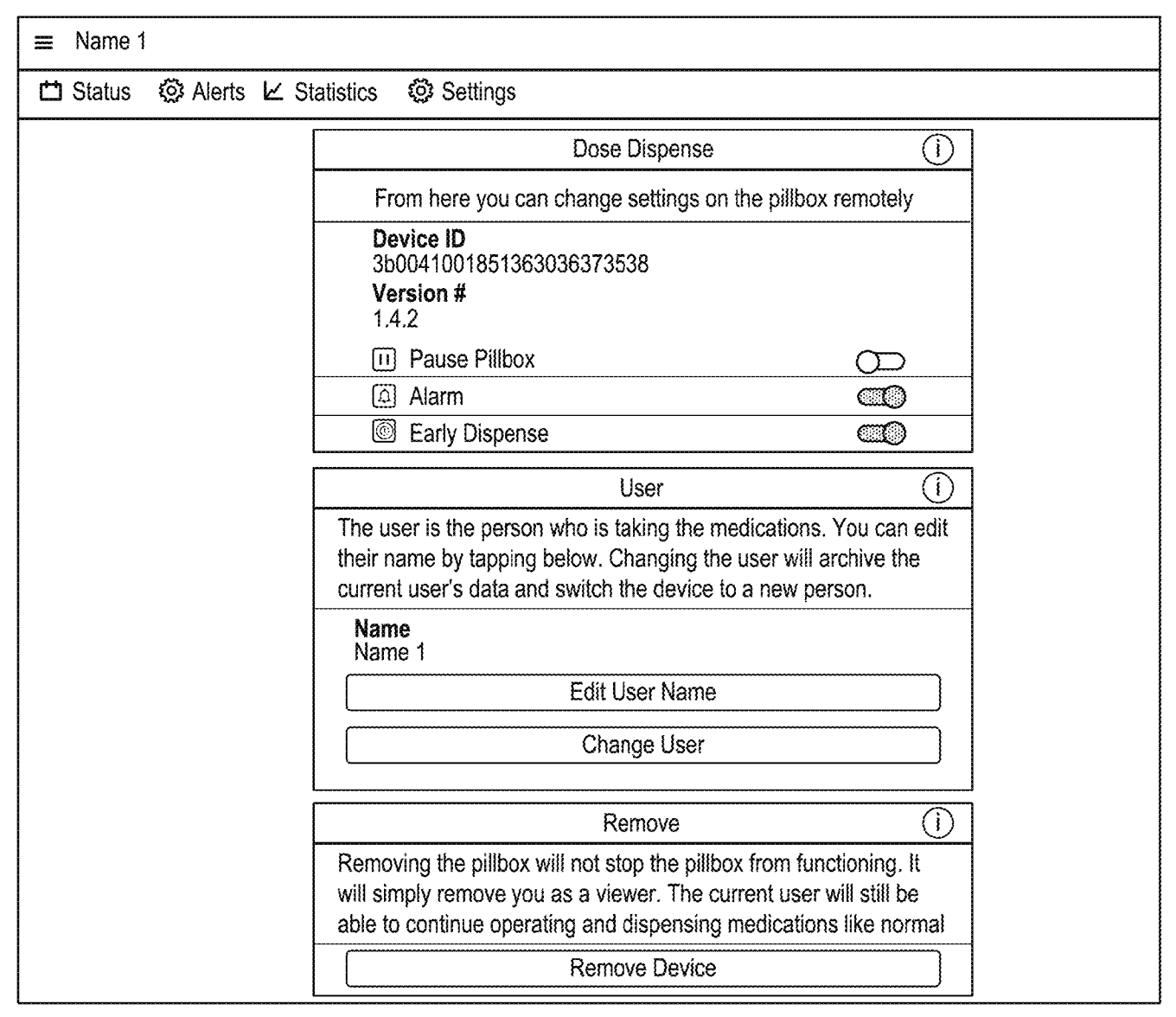

FIG. 15 shows settings associated with a user ("Name 1"). The setting shown in the GUI of FIG. 15 include whether the pillbox can be paused, whether the pillbox will emit an alarm when a medication is missed, and whether early dispensing is permitted. The settings in the GUI of FIG. 15 can be modified by a user in some embodiments, or alternatively they can be accessible only to a medical professional such as a doctor or pharmacist. The user can adjust several settings that are also available to change on the pillbox itself. Changing the pillbox user's name is also an option, as well as removing the device completely from the Dose Anywhere account the device is being viewed under.

Figure 16:
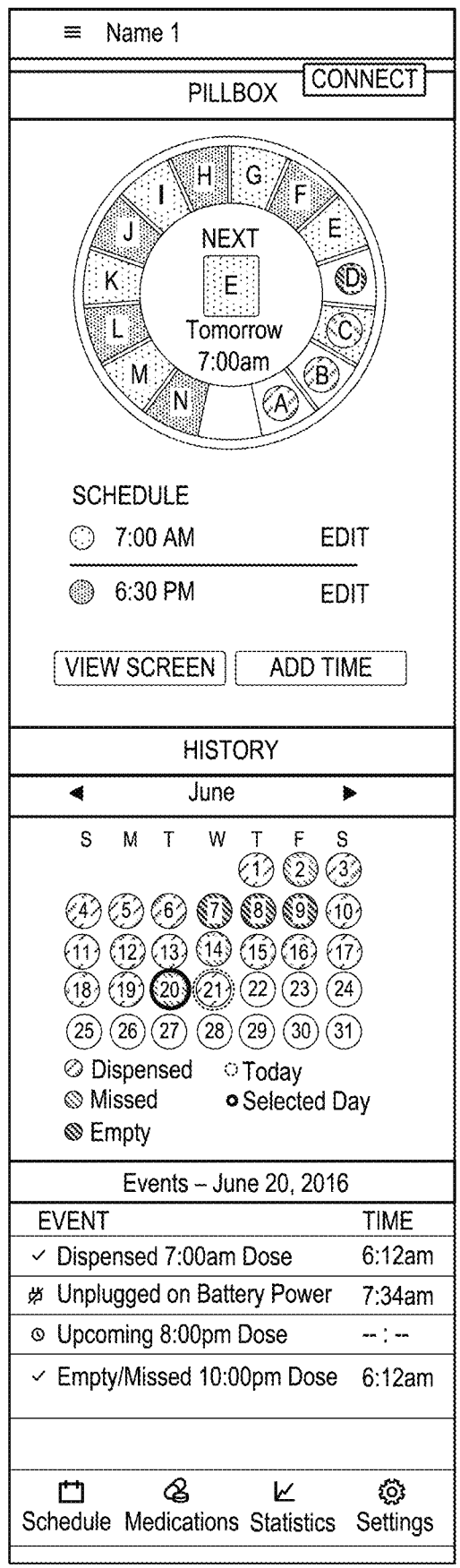

FIG. 16 is a GUI on a Dose Anywhere app that can be viewed on a smartphone, tablet, or other screen with reduced size. The GUI shown in FIG. 16 provides the user with much of the same information and metrics as the desktop version described above with respect to FIGS. 11-15, but the contents are optimized for a smaller screen. The four tabs at the bottom may read, from right to left, "Status," "Alerts," "Statistics," and "Settings" just as they do on the desktop version. A small-screen version can be helpful for users who are traveling and may not have access to a full-sized computer screen, for example.

Figure 17:
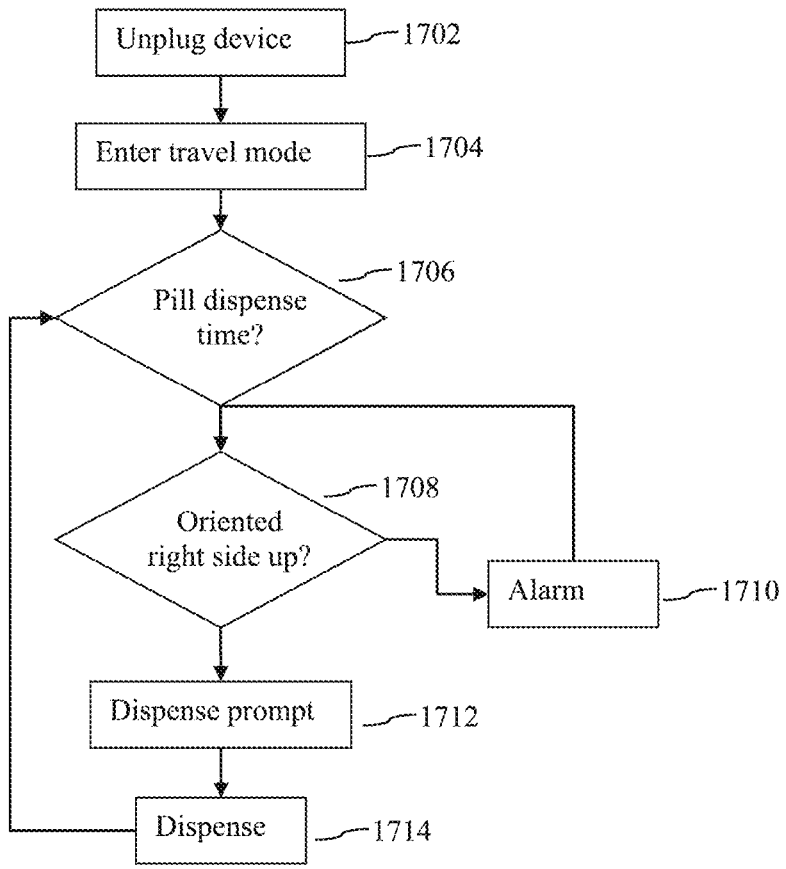
FIG. 17 is a flowchart of a travel mode operation scheme, according to an embodiment.
Figure 18:
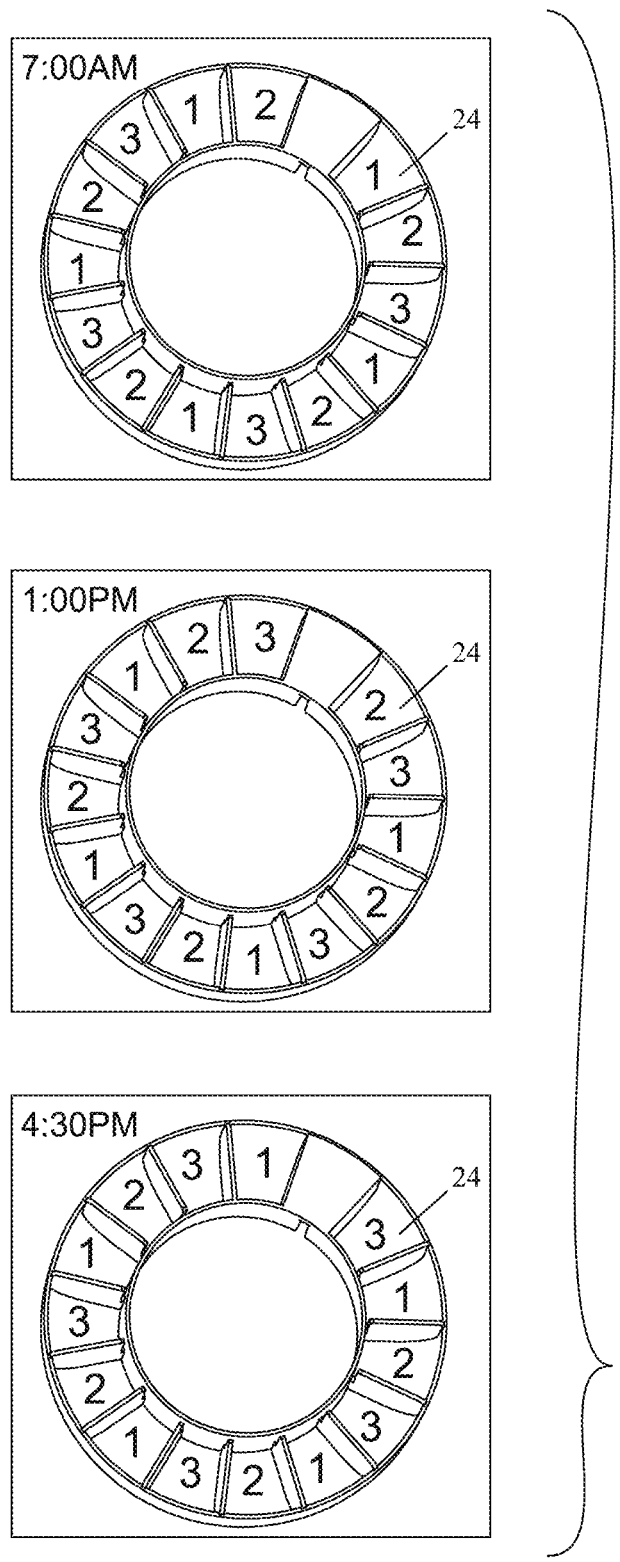
FIG. 18 is an example of a medication dispensing regimen at different time intervals.

FIG. 17 is a flowchart of a travel mode method 1700. As shown in FIG. 17, the travel mode method 1700 begins when the device is unplugged at 1702. The device enters travel mode at 1704, which can include performing steps to reduce power demand, such as reducing screen brightness. In embodiments, there can be some delay before entering travel mode, such as about 30 seconds.

At 1706, during travel mode the device monitors for pill dispensing time. Once pill dispensing time is reached, the device may verify that the device is right side up at 1708. In other words, if the device is oriented such that pills would be dispensed were the aperture to be arranged at a particular bin, the device will not open and instead an alarm 1710 will sound. In other words, in travel mode the carousel will not automatically rotate when it is time to dispense to prevent pills from falling out while traveling. This check at 1708 for orientation need not be performed in all embodiments, such as where a dispense prompt 1712 is produced that requires a user to affirm that the pills can be dispensed. At 1714, the pills are dispensed and the device monitors for the next pill dispense time at 1706.

In embodiments, the device can still be accessed during travel mode despite power saving mechanisms. While the screen is typically kept dark in travel mode to save power, a touchscreen can detect a sustained or repeated input, for example a 5 or 10 second touch. Other inputs, such as partially unscrewing the lid, could also be used to reactivate the screen or other features during travel mode.

As described above, a portable, versatile pill dispensing system can be used in a variety of settings and for a variety of pill dispensing regimens. For example, a simple and portable device is described with respect to FIGS. 1-5, a system configured for intuitive loading is described with respect to FIGS. 5-9, a system configured for early dispense and flexible scheduling is described with respect to FIG. 10, the Dose Anywhere platform for monitoring user compliance with a predetermined medication regimen is described above with respect to FIGS. 11-16, and travel mode is described above with respect to FIG. 17. It should be recognized that these embodiments are not exclusive, and that any particular device could incorporate any one or more of these. In some embodiments any subset, including all up to all of these features, can be embodied in a single device. No feature described herein is exclusive with any other, and unless explicitly stated to the contrary it should be understood that all of the components and subcomponents of each device and method described herein could be used interoperably with all other components and subcomponents of the other devices and methods described herein.

According to one embodiment, an automated pill dispensing device includes a base and a lid configured to mechanically engage with the base, the lid defining an aperture. The automated pill dispenser includes a carousel configured to be arranged between the base and the lid when the base and the lid are mechanically engaged, the carousel defining a plurality of bins each having a size corresponding to that of the aperture, the carousel further defining a slot, and the carousel having a zero position indicator with a size corresponding to that of the aperture. A motor is affixed to the base and also coupled to a tooth, wherein the tooth is configured to mechanically engage with the slot of the carousel. It should be understood that the motor could include a motor housing and could also be coupled to an input device or other componentry.

The automated pill dispensing device can further comprise a touchscreen, wherein the lid comprises a second aperture such that the touchscreen is accessible when the lid is mechanically engaged with the base. The touchscreen could be rectangular, circular, or another shape. The automated pill dispensing device can include a plurality of bins that each define a gap and the zero position indicator can define a gap end (see, e.g., FIG. 1H). The automated pill dispensing system can further comprise an indicator strip configured to fit within the gaps corresponding to the plurality of bins.

The automated pill dispensing system can further comprise a button that is configured to be depressed when the lid is mechanically engaged with the base. The button can be coupled to the motor or a housing of the motor, in embodiments. The automated pill dispensing system can further include a locking feature, such as a screw (which can in turn have an uncommon head to prevent unauthorized opening of the lid).

According to another embodiment, a method for early dispensing a medication for a system is disclosed. The method comprises providing an automated pill dispensing system as described in the preceding three paragraphs. The method further includes using the touchscreen or other input device to navigate to an early dispense option, dispensing the medications associated with a particular bin of the plurality of bins before an associated dispensing time has occurred, and applying a software lock to prevent dispensing a subsequent medication before its associated dispensing time.

According to another embodiment, a method for dispensing medication in a travel mode is disclosed. The method comprises:
(a) providing an automated pill dispensing system as described in the preceding four paragraphs;
(b) activating travel mode;
(c) determining when a pill dispensing time for one of the plurality of bins occurs,
(d) prompting the user, via the touchscreen, to dispense the medication;
(e) detecting that the medication has been dispensed; and
(f) repeating steps (c) through (e) until all of the medication is dispensed or until the user leaves travel mode.

The method can further include determining whether the automated pill dispensing system is oriented right side up between (c) and (d). The method can further include producing an alarm if the automated pill dispensing system is not oriented right side up between (c) and (d). The method can further include activating travel mode comprises unplugging the automated pill dispensing system.

According to another embodiment, a method for determining compliance with a predetermined medication regimen is disclosed. The method includes providing an automated pill dispensing system as described in the preceding paragraphs, providing a graphical user interface remote from the automated pill dispensing system, and displaying, at the graphical user interface, information indicative of whether a user has complied with the predetermined medication regimen.

The method can further include sending an alert based on an event selected from the group consisting of: pills dispensed, pills missed, refill needed, and pills waiting to be taken. The method can further include sending the alert to a phone number, an email address, or both.

In embodiments, the systems described herein or their components or subsystems can include computing devices, microprocessors, modules and other computer or computing devices, which can be any programmable device that accepts digital data as input. Such systems or subsystems and components can be configured to process the input according to instructions or algorithms, and provides results as outputs. In one embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In one embodiment, volatile memory can include random access memory (RAM), dynamic random access memory (DRAM), or static random access memory (SRAM), for example. In one embodiment, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

In one embodiment, the system or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application specific integrated circuit (ASIC) or field-10 programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method for early dispensing a medication for a system, the method comprising:
  (a) providing an automated pill dispensing system, the automated pill dispensing system comprising:
    a base;
    a lid configured to mechanically engage with the base, the lid defining an aperture;
    a carousel configured to be arranged between the base and the lid when the base and the lid are mechanically engaged,
      the carousel defining a plurality of bins each having a size corresponding to that of the aperture,
      the carousel defining a slot; and
    a motor affixed to the base and also coupled to a tooth, wherein the tooth is configured to mechanically engage with the slot of the carousel;
  (b) receiving a prompt to enter an early dispense mode;
  (c) dispensing the medication associated with a particular bin of the plurality of bins before an associated dispensing time has occurred; and
  (d) automatically, in the early dispense mode, applying a software lock to prevent dispensing a subsequent medication before its associated dispensing time.

2. The method of claim 1, wherein the carousel of the automated pill dispensing system has a zero position indicator with a size corresponding to that of the aperture.

3. The method of claim 1, wherein the plurality of bins each define a gap and the zero position indicator defines a gap end.

4. The method of claim 1, wherein the automated pill dispensing system further comprises an indicator strip configured to fit within gaps located between the walls of each of the plurality of bins and a center of the carousel, the indicator strip corresponding to the plurality of bins.

5. The method of claim 1, wherein the automated pill dispensing system further comprises a button that is configured to be depressed when the lid is mechanically engaged with the base.

6. The method of claim 5, wherein the button is coupled to the motor.

7. The method of claim 1, wherein the automated pill dispensing system further comprises a locking feature.

8. The method of claim 1, further comprising the step of verifying the early dispense of the medication.

9. The method of claim 1, wherein the automated pill dispensing system is connected to a wireless, cellular, or BLE network.

10. The method of claim 1, wherein the automated pill dispensing system connects to a wireless network and communicates medication dispensing adherence to a medical professional, care giver, family member, patient, or other person.

11. The method of claim 1, further comprising the step of sensing an early dispense of the medication after step (c) or (d).

12. The method of claim 11, further comprising the step of sending an alert after the early dispense.

13. The method of claim 12, wherein the alert is sent to a phone number.

14. The method of claim 12, wherein the alert is sent by email.

15. The method of claim 1, wherein the automated pill dispensing system further comprises a microprocessor, a memory, or both the microprocessor and the memory.

16. The method of claim 1, wherein the automated pill dispensing system is communicatively coupled to a user account.

17. The method of claim 16, wherein the user account stores data associated with one or more automated pill dispensing systems.

18. The method of claim 17, wherein the data comprises one or more of a status of each of the plurality of bins, a medication dispensing schedule, a connection status of the one or more automated pill dispensing systems, and an adherence rate.

19. The method of claim 18, wherein the data is accessed when a user selects one or more automated pill dispensing systems within the user account.

* * * * *